(12) United States Patent
Sugita

(10) Patent No.: US 8,016,753 B2
(45) Date of Patent: Sep. 13, 2011

(54) ENDOSCOPE

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 1097 days.

(21) Appl. No.: 11/422,721

(22) Filed: Jun. 7, 2006

(65) Prior Publication Data

US 2006/0281973 A1    Dec. 14, 2006

(30) Foreign Application Priority Data

| Jun. 9, 2005 | (JP) | P2005-169033 |
| Jun. 13, 2005 | (JP) | P2005-171936 |
| Jun. 13, 2005 | (JP) | P2005-171937 |
| Jun. 14, 2005 | (JP) | P2005-173152 |

(51) Int. Cl.
*A61B 1/12* (2006.01)

(52) U.S. Cl. .......... 600/156; 600/127; 600/129

(58) Field of Classification Search .......... 600/127, 600/129, 156–158, 169, 175
See application file for complete search history.

(56) References Cited

U.S. PATENT DOCUMENTS

| 4,281,646 A * | 8/1981 | Kinoshita | 600/157 |
| 4,436,087 A * | 3/1984 | Ouchi | 600/106 |
| 4,667,656 A * | 5/1987 | Yabe | 600/109 |
| 4,878,893 A * | 11/1989 | Chin | 604/21 |
| 5,207,213 A * | 5/1993 | Auhll et al. | 600/104 |
| 5,464,008 A * | 11/1995 | Kim | 600/157 |
| 5,630,795 A * | 5/1997 | Kuramoto et al. | 604/30 |
| 5,647,840 A * | 7/1997 | D'Amelio et al. | 600/169 |
| 5,733,243 A * | 3/1998 | Yabe et al. | 600/121 |
| 5,944,654 A * | 8/1999 | Crawford | 600/157 |
| 5,989,183 A * | 11/1999 | Reisdorf et al. | 600/156 |
| 6,354,992 B1 * | 3/2002 | Kato | 600/157 |
| 6,409,657 B1 * | 6/2002 | Kawano | 600/157 |
| 6,595,915 B2 * | 7/2003 | Akiba | 600/157 |
| 6,638,214 B2 * | 10/2003 | Akiba | 600/157 |
| 6,699,185 B2 * | 3/2004 | Gminder et al. | 600/157 |
| 6,712,757 B2 * | 3/2004 | Becker et al. | 600/121 |
| 6,814,728 B2 | 11/2004 | Ouchi | |
| 6,953,430 B2 | 10/2005 | Kidooka | |
| 7,472,847 B2 | 1/2009 | Mukai et al. | |
| 2001/0004692 A1 | 6/2001 | Kidooka et al. | |
| 2004/0186348 A1 | 9/2004 | Kidooka | |

(Continued)

FOREIGN PATENT DOCUMENTS

JP    55-002407    1/1980

(Continued)

OTHER PUBLICATIONS

English Language Abstract of JP 2001-292958.

(Continued)

*Primary Examiner* — Matthew J Kasztejna

(74) *Attorney, Agent, or Firm* — Greenblum & Bernstein P.L.C.

(57) ABSTRACT

An endoscope including an inserted portion, which is adapted to be inserted into an organ, having a distal portion with a distal surface, a liquid outlet, which is formed in the distal portion, and is adapted to eject liquid therefrom toward an object located in vicinity to the distal portion, and a flow attracting member, which is adapted to attract a flow of the liquid ejected from the liquid outlet, is provided. The flow of the liquid ejected from the liquid outlet is angled by the flow attracting member so that the liquid is directed at a predetermined portion of the object.

24 Claims, 26 Drawing Sheets

U.S. PATENT DOCUMENTS

| | | |
|---|---|---|
| 2004/0195398 A1 | 10/2004 | Mukai et al. |
| 2004/0210284 A1 | 10/2004 | Okada |
| 2006/0155271 A1 | 7/2006 | Sugita et al. |
| 2006/0178656 A1 | 8/2006 | Sugita et al. |
| 2006/0178657 A1 | 8/2006 | Sugita et al. |
| 2006/0178669 A1 | 8/2006 | Sugita et al. |

FOREIGN PATENT DOCUMENTS

| | | |
|---|---|---|
| JP | 63-130717 | 8/1988 |
| JP | 5-207962 | 8/1993 |
| JP | 6-292685 | 10/1994 |
| JP | 8-191791 | 7/1996 |
| JP | 8-286127 | 11/1996 |
| JP | 10-165359 | 6/1998 |
| JP | 2001-292958 | 10/2001 |
| JP | 2003-24346 | 1/2003 |
| JP | 2003-153851 | 5/2003 |
| JP | 2004-049452 | 2/2004 |
| JP | 2004-174157 | 6/2004 |
| JP | 2004-275548 | 10/2004 |
| JP | 2004-275985 | 10/2004 |
| JP | 2004-313537 | 11/2004 |
| JP | 2004-314524 | 11/2004 |
| JP | 3758769 | 1/2006 |
| JP | 2006-187474 | 7/2006 |
| JP | 2006-187475 | 7/2006 |
| JP | 2006-345888 | 12/2006 |

OTHER PUBLICATIONS

English Language Abstract of JP 6-292685.
English Language Abstract of JP 2004-049452.
Japan (JP Appl. No. 2005-173152) Office action, dated Jan. 6, 2011 along with an english translation thereof.
Japan (JP Appl. No. 2005-171936) Office action, dated Jan. 6, 2011 along with an english translation thereof.

* cited by examiner

| e | FLOW DIRECTION |
|---|---|
| 0.25mm | UNSTABLE |
| 0.3mm | CHANGES WHEN L ≧ 0.5mm |
| 0.4mm | CHANGES WHEN L ≧ 0.8mm |
| 0.5mm | CHANGES WHEN L ≧ 1mm |
| 0.7mm | NO CHANGE |

ENDOSCOPE

BACKGROUND OF THE INVENTION

The present invention relates to an endoscope, and particularly to an endoscope capable of directing liquid ejected from a tip end thereof at a predetermined angle.

Generally, an endoscope unit is provided with a liquid channel arranged in parallel with an axis of the endoscope, through which liquid such as water is conveyed, and an aperture at a front end thereof to outlet the liquid, so that an object region to be observed, having body fluid, blood, and the like thereon, can be cleaned with the liquid injected through the aperture. Examples of such an endoscope unit with an aperture at a distal end thereof is disclosed in Japanese Patent Provisional Publication Nos. 2001-292958 and BE16-292685. The endoscope unit disclosed in the former publication is provided with an aperture that is opened to a straight front of a distal portion of the endoscope unit. The endoscope unit disclosed in the latter publication is provided with a treatment tool to be inserted through an instrument channel of the endoscope, which is equipped at a distal portion of an insulated flexible sheath. The treatment tool includes a high-frequency electrode, which is protrusible from the distal portion of the sheath, to incise or coagulate mucous membrane of in vivo tissues, and an aperture is formed on a distal surface of the distal portion, through which water to clean the mucous membrane is ejected.

In such configurations, however, the water through the aperture is simply ejected toward the straight front, and not ejected toward a center of a scope of observation, as the aperture is provided in an offset position with respect to an axis of the distal portion of the endoscope unit. Therefore, it is difficult to aim the water at a portion of the mucous membrane to be cleaned. In order to aim the water at the portion to be cleaned, an entire inserted portion is required to be shifted. In this case, the scope of observation is shifted as well, and thus it is still difficult to aim the water at the portion to be cleaned, and removing the body fluid from the mucous membranes is often time-consuming.

In consideration of the above, the aperture may be arranged in an oblique orientation with respect to the axis of the inserted portion, so that the water therethrough can be ejected in an angled direction. With this configuration, the water may be ejected to the center of the scope of observation when the aperture is spaced from the aimed portion of the mucous membrane for a predetermined distance. However, once the aperture is spaced from the aimed portion for a greater or a smaller distance, the ejected water does not meet the center of the observation scope. Further, as the aperture arranged in the oblique orientation requires greater space in the distal portion, other features of the endoscope may be limited. In an endoscope unit with a treatment tool, such as disclosed in the latter publication, a diameter of the treatment tool is generally configured to be approximately in a range from 2 to 3 mm. Therefore, arranging the aperture in the oblique orientation in the range is even more difficult. Thus, configuring the distal portion of the endoscope unit to allow the water therethrough to be ejected in a desired direction has been difficult.

SUMMARY OF THE INVENTION

The present invention is advantageous in that an endoscope with a distal portion, in which liquid ejected from an aperture of the endoscope can be directed in a predetermined direction, is provided. With the distal portion of the endoscope, the liquid can be ejected at a center of a scope of the observation.

According to an aspect of the present invention, there is provided an endoscope, including an inserted portion, which is adapted to be inserted into an organ, having a distal portion with a distal surface, a liquid outlet, which is formed in the distal portion, and is adapted to eject liquid therefrom toward an object located in vicinity to the distal portion, and a flow attracting member, which is adapted to attract a flow of the liquid ejected from the liquid outlet. The flow of the liquid ejected from the liquid outlet is angled by the flow attracting member so that the liquid is directed at a predetermined portion of the object.

Optionally, the flow attracting member may be arranged in the distal portion in a position adjacent to the liquid outlet to protrude from the distal surface of the inserted portion.

Optionally, the liquid outlet may be oriented in parallel with an axis of the inserted portion.

Optionally, the distal surface of the inserted portion may be provided with an observation window to capture an image of the object. The flow attracting member may be arranged on the distal surface of the inserted portion in a position between the liquid outlet and the observation window, so that the liquid ejected from the liquid outlet is attracted to the flow attracting member and the flow of the liquid can be angled toward a front of the observation window.

Optionally, the flow attracting member may be formed to be a pin to protrude forwardly from the distal surface of the inserted portion.

Optionally, a recessed portion may be formed in the distal portion. The liquid outlet may be arranged in the recessed portion on a plane in parallel with the distal surface of the inserted portion. One of side surfaces of the recessed portion which is perpendicular to the distal surface of the inserted portion may be the flow attracting member.

Optionally, a portion of the one of the side surfaces of the recessed portion may be formed to be bossed toward a straight front of the liquid outlet.

Optionally, the flow attracting member may be adapted to be protrusible and retractable in an axial direction of the inserted portion, so that a flow of the liquid ejected from the liquid outlet is angled in correspondence to protrusion and retraction of the flow attracting member.

Optionally, the flow attracting member may be adapted to be protruded and retracted by a remote operation.

Optionally, the flow attracting member may be formed to be a protrusible pin to be protruded forwardly and retracted inwardly from the distal surface of the inserted portion.

Optionally, the flow attracting member includes a plurality of pins arranged in vicinity to the liquid outlet. At least one of the plurality of pins may be selectively protruded and retracted from the distal surface of the inserted portion.

Optionally, the flow attracting member may be adapted to be shifted along the distal surface of the inserted portion so that a flow of the liquid ejected from the liquid outlet is shifted in correspondence to movements of the flow attracting member Optionally, the flow attracting member may be formed to be a pin to protrude forwardly from the distal surface of the inserted portion, and may be adapted to rotate about an axis.

Optionally, the flow attracting member may be adapted rotate around the liquid outlet.

Optionally, the flow attracting member may be shifted by a remote operation to an operation wire, which is adapted to be forwarded and retracted.

Optionally, the flow attracting member may be shifted by drive force from a motor equipped in the distal portion.

Optionally, a distance between the Liquid outlet and the flow attracting member may be 0.5 mm at a maximum.

Optionally, the distance between the liquid outlet and the flow attracting member may be in a range from 0.3 mm to 0.5 mm.

Optionally, the endoscope may further include a treatment tool having a sheath to be inserted through an insertion channel of the endoscope, and a rod-like high-frequency electrode, which is adapted to be protrusiblk and retractable in an axial direction of the sheath from a distal surface of the sheath. The high-frequency treatment tool may be adapted to serve as the flow attracting member, and the flow of the liquid ejected from the liquid outlet may be angled by the high-frequency electrode when the high-frequency electrode is protruded from the distal surface of the sheath.

Optionally, the liquid outlet may be arranged adjacent to the high-frequency electrode with a predetermined distance therebetween.

Optionally, the flow of the liquid ejected from the liquid outlet may be directed toward a straight front of the liquid outlet when the high-frequency electrode is retracted from the distal surface of the sheath.

Optionally, the distance between the liquid outlet and the high-frequency electrode may be 0.5 mm at a maximum, Optionally, the distance between the liquid outlet and the high-frequency electrode may be in a range from 0.3 mm to 0.5 mm.

Optionally, a liquid channel to convey the liquid being ejected from the liquid outlet may be formed in the sheath in parallel with an axis of the sheath. A diameter of the liquid channel may be configured to be constant in a distal portion of the sheath. The liquid channel may be in communication with the liquid outlet, which is oriented in parallel with the axis of the sheath.

Optionally, the sheath may be configured to be a flexible multi-lumen tube including a plurality of lumens, which are formed to extend in parallel with the axis of the sheath throughout an entire length of the sheath. One of the plurality of lumens may be adapted to be the liquid channel.

According to an aspect of the present invention, there is provided a high-frequency treatment tool for an endoscope, including a sheath having a distal surface, which is adapted to be inserted through an insertion channel of the endoscope, a rod-like high-frequency electrode, which is adapted to be protrusible and retractable in an axial direction of the sheath from the distal surface of the sheath, a liquid outlet, which is formed on the distal surface of the sheath adjacently to the high-frequency electrode, and is adapted to eject liquid therefrom toward an object located in vicinity to the distal surface. A flow of the liquid ejected from the liquid outlet is angled by the high-frequency electrode when the high-frequency electrode is protruded so that the liquid is directed at a predetermined portion of the object.

Optionally, the liquid outlet may be arranged adjacent to the high-frequency electrode with a predetermined distance therebetween.

Optionally, the flow of the liquid ejected from the liquid outlet may be directed toward a straight front of the liquid outlet when the high-frequency electrode is retracted from the distal surface of the sheath.

Optionally, the distance between the liquid outlet and the high-frequency electrode may be 0.5 mm at a maximum.

Optionally, the distance between the liquid outlet and the high-frequency electrode may be in a range from 0.3 mm to 0.5 mm.

Optionally, a liquid channel to convey the liquid being ejected from the liquid outlet may be formed in the sheath in parallel with an axis of the sheath. A diameter of the liquid channel may be configured to be constant in a distal portion of the sheath. The liquid channel may be in communication with the liquid outlet, which is oriented in parallel with the axis of the sheath.

Optionally, the sheath may be configured to be a flexible multi-lumen tube including a plurality of lumens, which are formed to extend in parallel with the axis of the sheath throughout an entire length of the sheath. One of the plurality of lumens may be adapted to be the liquid channel.

DETAILED DESCRIPTION OF THE EMBODIMENTS

Hereinafter, referring to the accompanying drawings, an endoscope according to illustrative embodiments of the invention will be described.

First Embodiment

Figure 1:
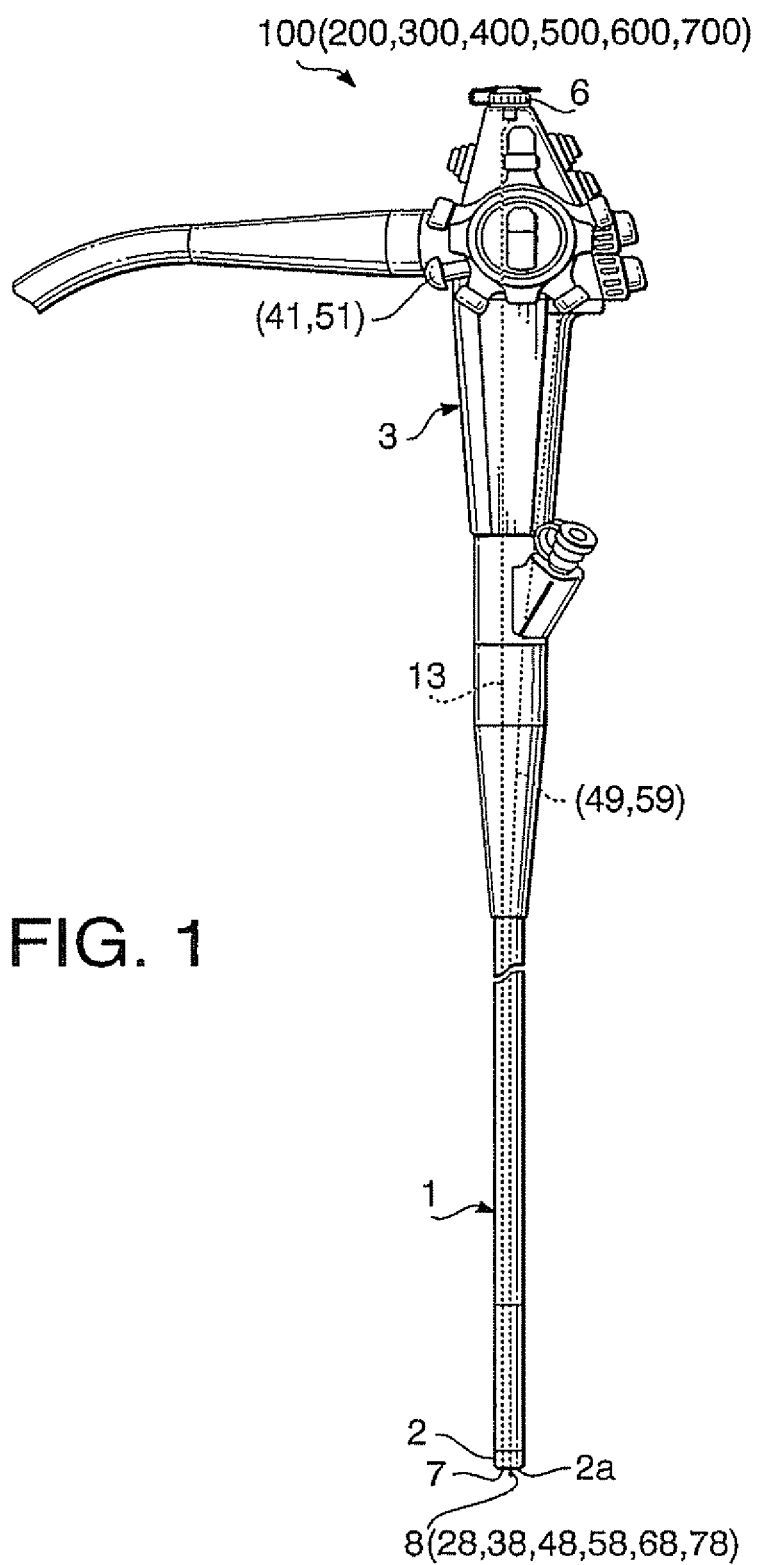
FIG. 1 is an external view of an entire configuration of an endoscope according to a first embodiment of the present invention.

FIG. 1 is an external view of an entire configuration of an endoscope 100 according to a first embodiment of the present invention, The endoscope 100 includes a flexible inserted portion 1) a tip portion 2, within which an objective optical system 9 (see FIG. 3) is included, at a distal end of the inserted portion 1, and an operation unit 3, which is connected to a proximal end of the inserted portion 1. On a proximal end of the operation unit 3, a liquid filler port 6 is provided, so that liquid to be used for cleaning a region of a mucous membrane is injected through the liquid filler port 6.

Figure 2:
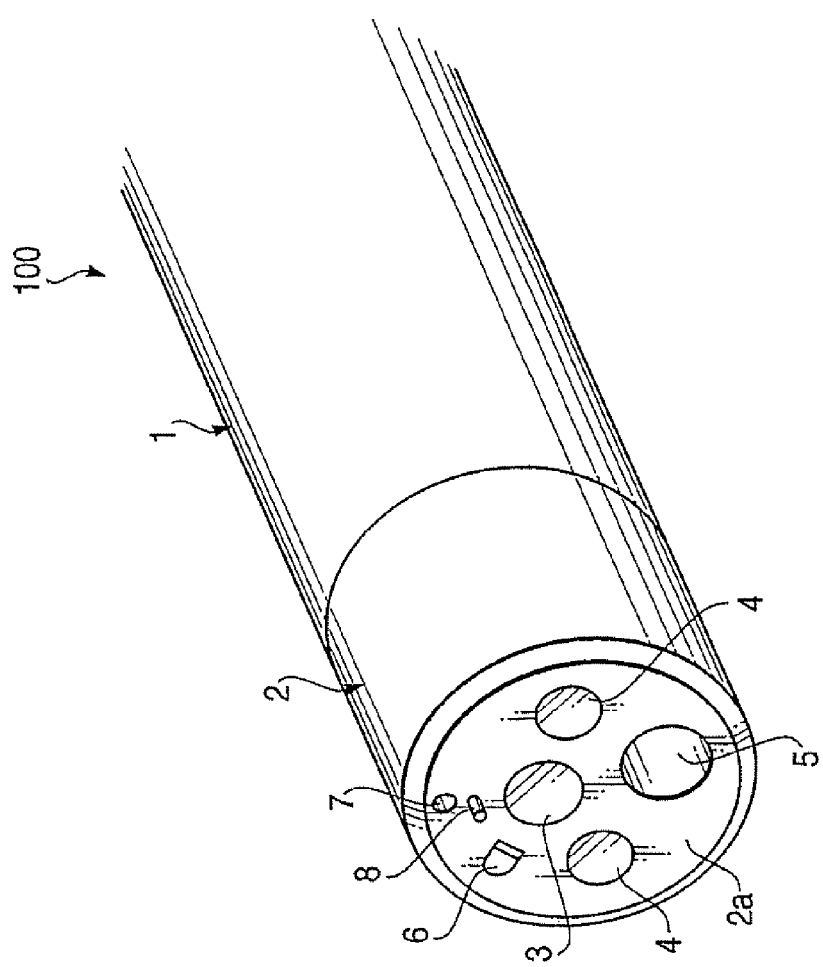
FIG. 2 is a perspective view of a tip portion of the endoscope according to the first embodiment of the invention.

FIG. 2 is a perspective view of the tip portion 2 of the endoscope 100 according to the first embodiment of the invention. The tip portion 2 includes a distal surface 2a, on which an observation window 3 and an illumination window 4, an instrument outlet 5, and a fluid nozzle 6 are arranged. An image of a region inside a body to be observed is captured through the observation window 3, and the illumination window 4 is adapted to emit light to illuminate the region of observation. The instrument outlet 5 is provided to allow a treatment instrument (not shown) to protrude therefrom. An opening of the fluid nozzle 6 is directed to a surface of the observation window 3, so that fluid such as water and air from the fluid nozzle 6 is ejected toward the surface of the observation window 3.

The distal surface 2a is further provided with a liquid outlet 7. Liquid, for example water, to clean the observed region of mucous membrane is ejected from the liquid outlet 7 as the tip portion 2 is brought in front of the region to be observed. The liquid outlet 7 is opened to a straight front of the distal surface 2a of the tip portion 2.

Figure 3:
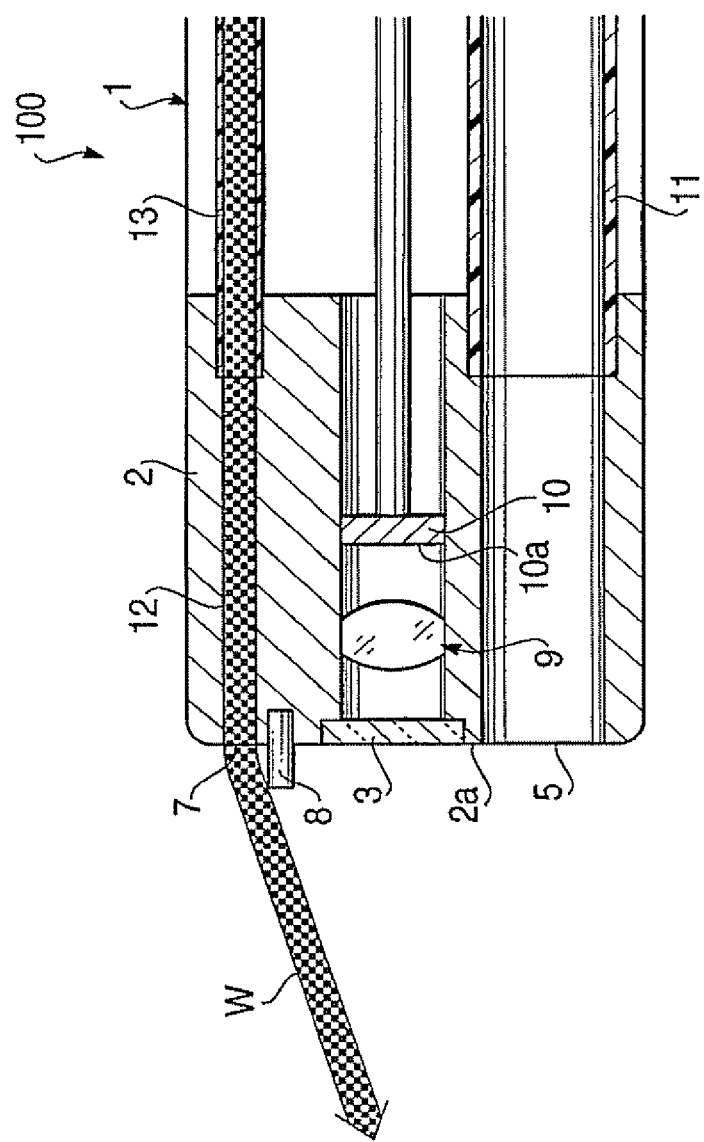
FIG. 3 is a cross-sectional side view of the tip portion of the endoscope according to the first embodiment of the invention.

Further, a protruded flow attracting pin 8, as a flow attracting member, is fixedly provided in vicinity to the liquid outlet 7 on the distal surface 2a. The flow attracting pin 8 is adapted to angle a direction of flow of the water being ejected from the liquid outlet 7 at a predetermined position adjacent to the liquid outlet 7, FIG. 3 is a cross-sectional side view of the tip portion 2 of the endoscope 100 according to the first embodiment of the invention. The tip portion 2 includes the objective optical system 9, which is arranged inside the observation window 3, and an image capturing element 10, which is arranged to have an image capturing area 10a thereof to be at a projecting position of the object projected through the objective optical system 9, so that an object in straight front of the tip portion 2 can be observed. Further, an instrument channel 11, which is in communication with the instrument outlet 5, is provided, and the treatment tool is inserted through the instrument channel 11 to be protruded from the instrument outlet 5.

A liquid channel 12 is formed to be in parallel with an axis of the tip portion 2, and a distal end thereof is formed to be the liquid outlet 7. A proximal end of the liquid channel 12 is in communication with a liquid supply tube 13 (see also FIG. 1), which is arranged inside the inserted portion 1. A cross-sectional area of the liquid channel 12 has a shape of a circle, and the liquid outlet 7 opened at the distal end of the liquid channel 12 has a shape of the circle as well.

The flow attracting pin 8 has a cross-sectional surface of a circle, for example, and is arranged to protrude perpendicularly to a cross-section of the tip portion 2. The flow attracting pin 8 is arranged adjacently to the liquid outlet 7 and in a position between the liquid outlet 7 and the observation window 3.

With this configuration, water W ejected from the liquid outlet 7 is attracted to the flow attracting pin 8, and a flow of the water W is angled toward a front of the observation window 3, so that the water W can be aimed at a center of an observed region to be cleaned. It should be noted that the water W is not diffused even when the flow thereof is angled, and a diameter of the water W corresponding to a diameter of the liquid outlet 7 is maintained steady until the water W strikes the portion of the mucous membrane to be cleaned, thus the mucous membrane can be cleaned effectively. An angle of the flow to be inclined (attracted) to the flow attracting pin 8 is for example in a range approximately from 5 degrees to 30 degrees, The above-described attraction of the water W toward the flow attracting pin 8, which is arranged in parallel with an original direction of the water W, is initially due to negative pressure caused between the flow attracting pin 8 and the water W flowing in parallel with the flow attracting pin 8. As the water W is attracted closely to the flow attracting pin 8, and finally becomes in contact with the flow attracting pin 8, the water W thereafter maintains the contact with the flow attracting pin 8 with an effect of surface tension.

Figures 4, 5:
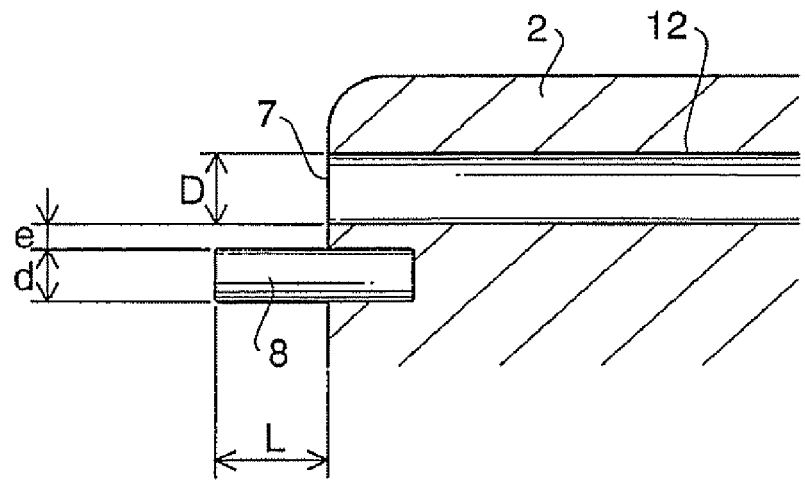
FIG. 4 is a cross-sectional partial side view to illustrate the tip portion of the endoscope according to the first embodiment of the invention.
FIG. 5 is a table to illustrate an result of an experiment according to the first embodiment of the invention.

FIG. 4 is a cross-sectional partial side view to illustrate the tip portion 2 of the endoscope 100, which is used in an experiment to define a relation between a distance e from the liquid outlet 7 to the flow attracting pin 8 and a length L of the flow attracting pin 8, according to the first embodiment of the invention. FIG. 5 is a table to illustrate an result of the experiment that defines the relation between the distance e and the length L, according to the first embodiment of the invention. In this experiment, a diameter of the flow attracting pin d is configured to be 0.33 mm, and the diameter D of the liquid outlet 7 is configured to be 0.5 mm.

As shown in FIG. 5, it is preferable that the distance e between the flow attracting pin 8 and the liquid outlet 7 is less than or equal to 0.5 mm (e≦0.5 mm). In addition, when the distance e is less than or equal to 0.25 mm (e≦0.25 mm), the direction of the flow of the ejected water W is unstable, and the flow can be angled even with the length L of the flow attracting pin 8 being considerably small. Therefore, the distance e is preferable to be in a range from 0.3 mm to 0.5 mm.

Second Embodiment

Figure 6:
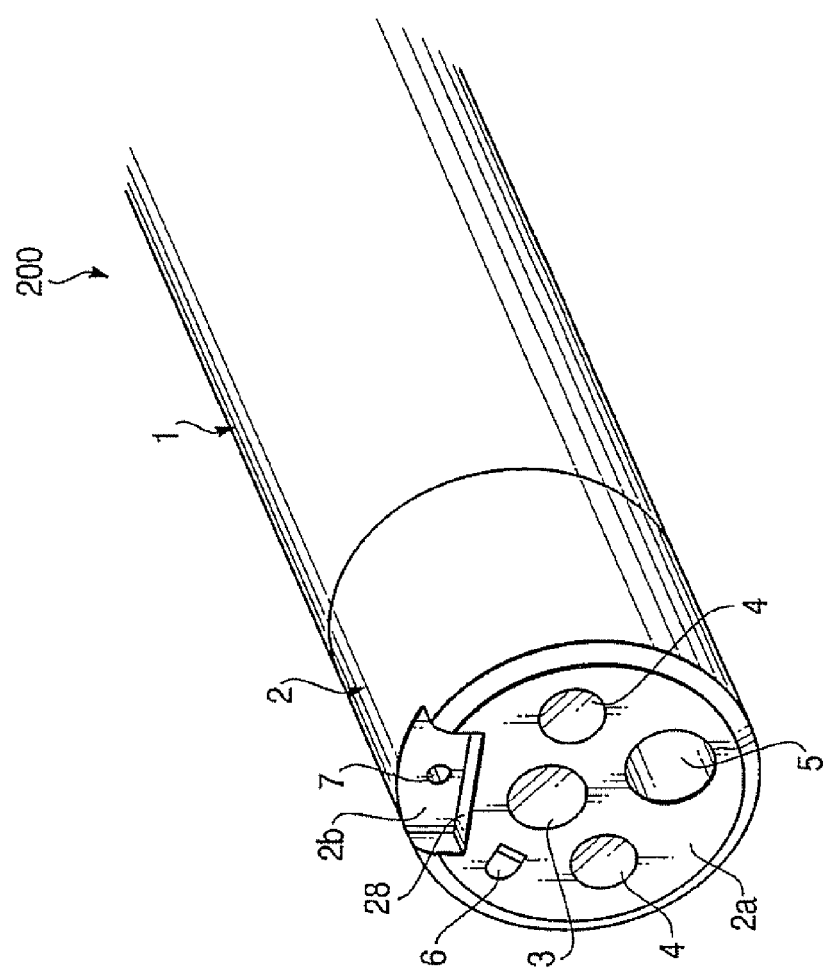
FIG. 6 shows a perspective view of a tip portion of an endoscope according to a second embodiment of the invention.
Figure 7:
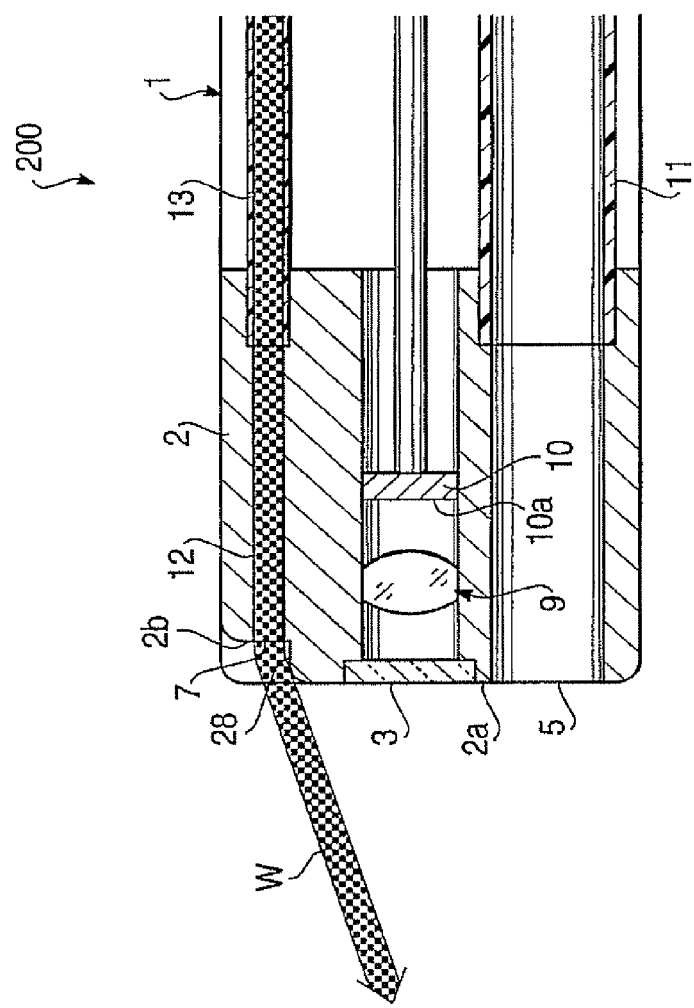
FIG. 7 shows a cross-sectional side view of the tip portion of the endoscope according to the second embodiment of the invention.

FIG. 6 shows a perspective view of a tip portion 2 of an endoscope 200 according to a second embodiment of the invention. FIG. 7 shows a cross-sectional side view of the tip portion 2 of the endoscope 200 according to the second embodiment of the invention. In the present and following embodiments, configurations corresponding to the configuration of the first embodiment is referred to by the identical reference numerals, and description of those is omitted.

As shown in FIGS. 6 and 7, the tip portion 2 is provided with a recessed portion 2b, which is formed on a distal surface 2a, A liquid outlet 7 is formed in the recessed portion 2b, on a plane in parallel with the distal surface 2a. With this configuration, a horizontal surface 28 in the recessed portion 2b, which is approximately perpendicular to the plane on which the liquid outlet 7 is formed, serves as the flow attracting member. Thus, water W ejected from the liquid outlet 7 is attracted toward the horizontal surface 28, and is angled toward a front of an observation window 3.

Third Embodiment

Figure 8:
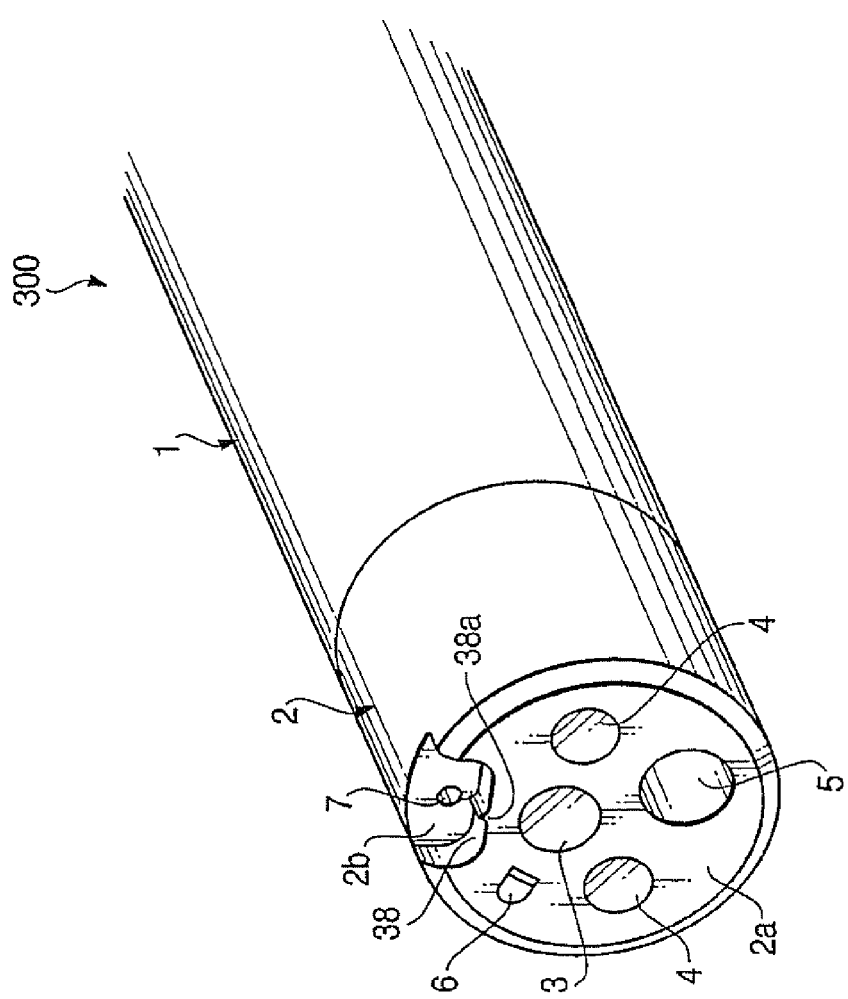
FIG. 8 shows a perspective view of a tip portion 2 of an endoscope according to a third embodiment of the invention.
Figure 9:
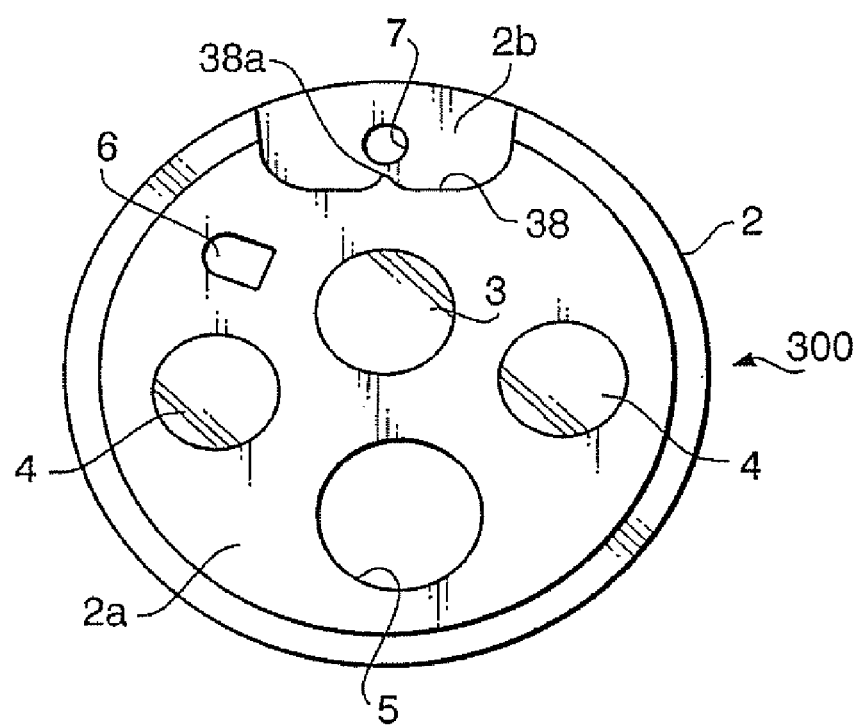
FIG. 9 shows a front view of the tip portion of the endoscope according to the third embodiment of the invention.

FIG. 8 shows a perspective view of a tip portion 2 of an endoscope 300 according to a third embodiment of the invention. FIG. 9 shows a front view of the tip portion 2 of the endoscope 300 according to the third embodiment of the invention. As shown in FIGS. 8 and 9, the tip portion 2 is provided with a recessed portion 2b, and a liquid outlet 7 is formed in the recessed portion 2b on a plane in parallel with a distal surface 2a. It should be noted that a center portion 38a of a horizontal surface 38 is formed to be bossed toward a straight front of the liquid outlet 7. With this configuration, the water W ejected from the liquid outlet 7 is stably angled toward a front of an observation window 3 without swinging.

Fourth Embodiment

Figure 10:
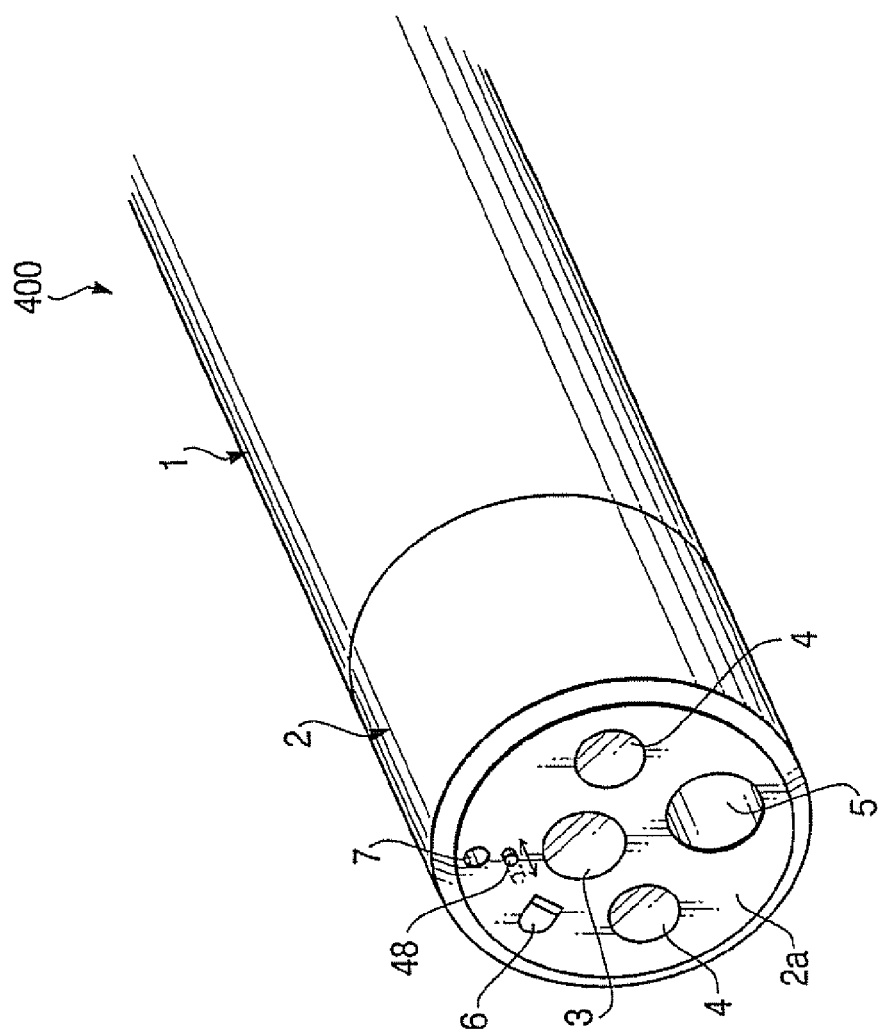
FIG. 10 shows a perspective view of a tip portion of an endoscope according to a fourth embodiment of the invention.
Figure 11:
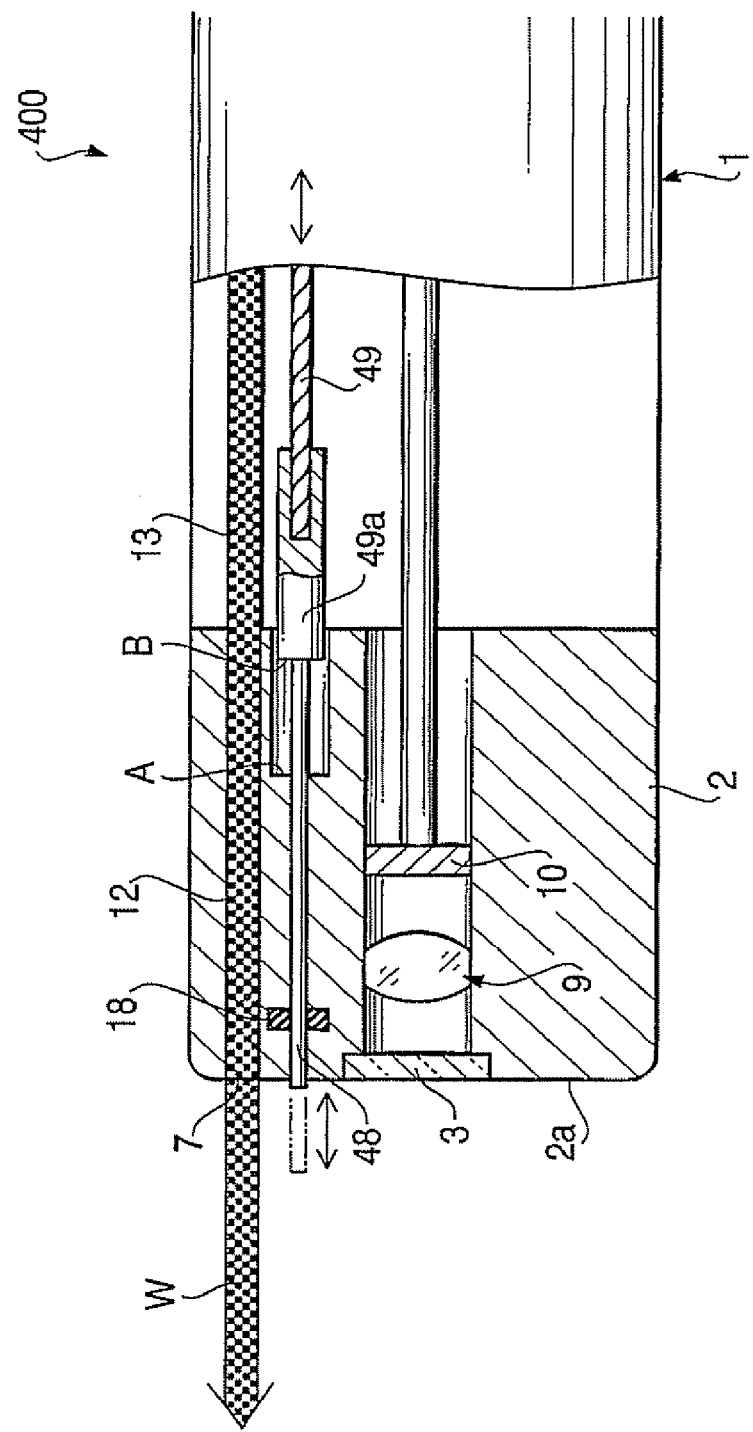
FIGS. 11 and 12 show cross-sectional side views of the tip portion of the fourth endoscope according to the fourth embodiment of the invention.
Figure 12:
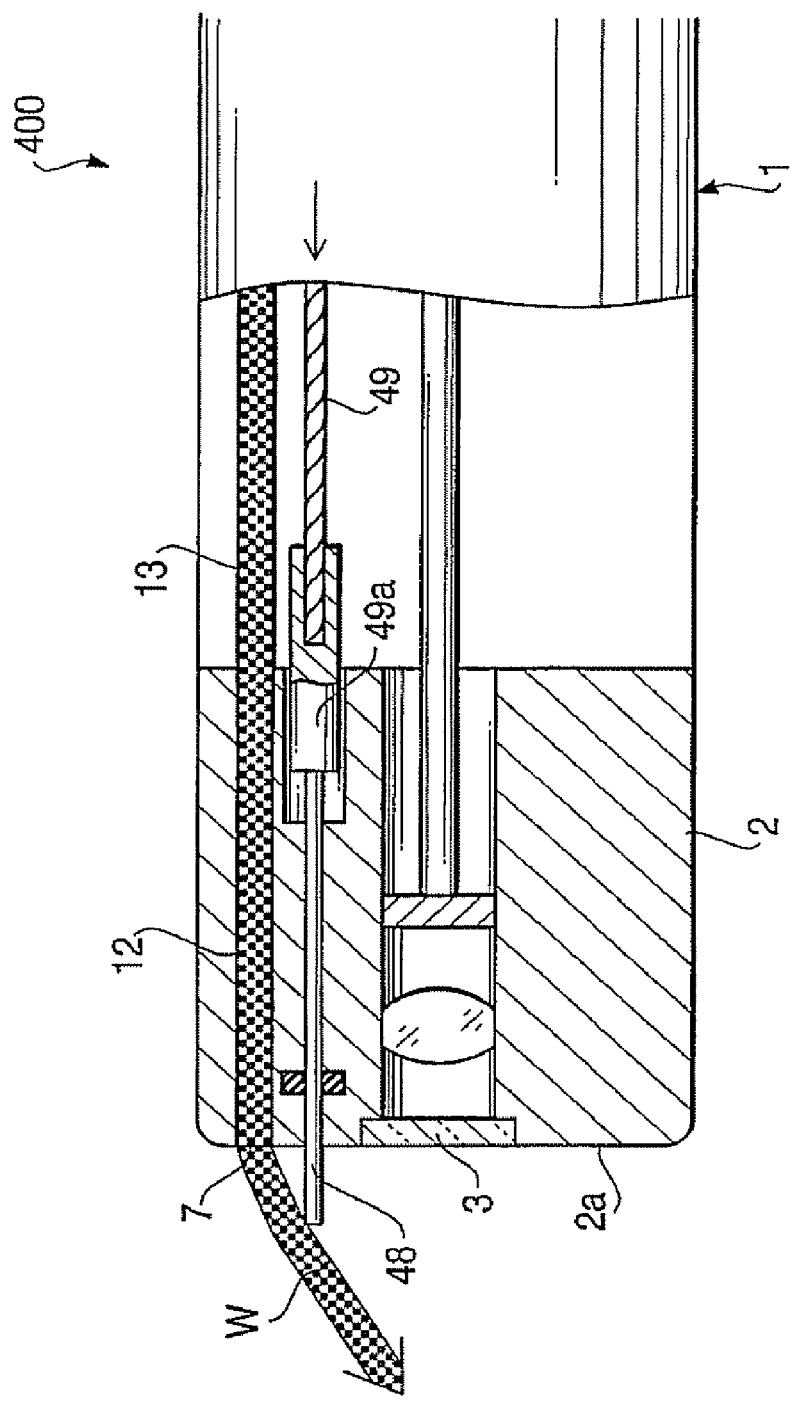

FIG. 10 shows a perspective view of a tip portion 2 of the endoscope 400 according to the fourth embodiment of the invention. FIGS. 11 and 12 show cross-sectional side views of the tip portion 2 of the endoscope 400 according to the fourth embodiment of the invention. A flow attracting pin 48, as a flow attracting member, is provided in vicinity to a liquid outlet 7 on a distal surface 2a of the tip portion 2. In the present embodiment, the flow attracting pin 48 is configured to be protruded and retracted in axial directions of the endoscope 400 by operations to an operation knob 41, which is provided to the operation unit 3. The operation knob 41 is connected to an operation wire 49, which is arranged inside the inserted portion 1, to be connected with a proximal end of the flow attracting pin 48, so that the operations to the operation knob 41 are conveyed to the flow attracting pin 48, and thus the flow attracting pin 48 can be protruded and retracted.

As shown in FIGS. 10 and 11, the flow attracting pin 48 is arranged adjacently to the liquid outlet 7 and in a position between the liquid outlet 7 and the observation window 3. The flow attracting pin 48 is configured to have a cross-section of a circle, and is adapted to be protruded and retracted from the distal surface 2a toward a straight front thereof. Further, an O-ring 18 is provided for sealing the flow attracting pin 48 inside the tip portion 2.

As the operation wire 49 is forwarded from the proximal end thereof, the flow attracting pin 48 is protruded as indicated in dotted lines in FIG. 11 from the distal surface 2a, and is retracted as indicated in the solid line in FIG. 11 as the operation wire 49 is pulled toward the proximal end thereof.

It should be noted that the operation wire 49 is provided with a stopper member 49a with a stopper surface B, which becomes in contact with a contact surface A when the operation wire 49 is forwarded to a predetermined length. In this configuration, the flow attracting pin 48 is configured not to be protruded further as the contact surface A and the stopper surface B are in contact with each other.

With the above configuration, when the flow attracting pin 48 is retracted from the distal surface 2a or is protruded only for a small length, as in indicated in the solid line in FIG. 11, water W through the liquid outlet 7 is ejected toward a straight front.

Further, as the flow attracting pin 48 is protruded from the distal surface 2a to an extent, as shown in FIG. 12, the water W ejected through the liquid outlet 7 is attracted to the flow attracting pin 48, so that the flow of the water W is directed to a center of an observed region of the mucous membrane to be cleaned.

Figure 13:
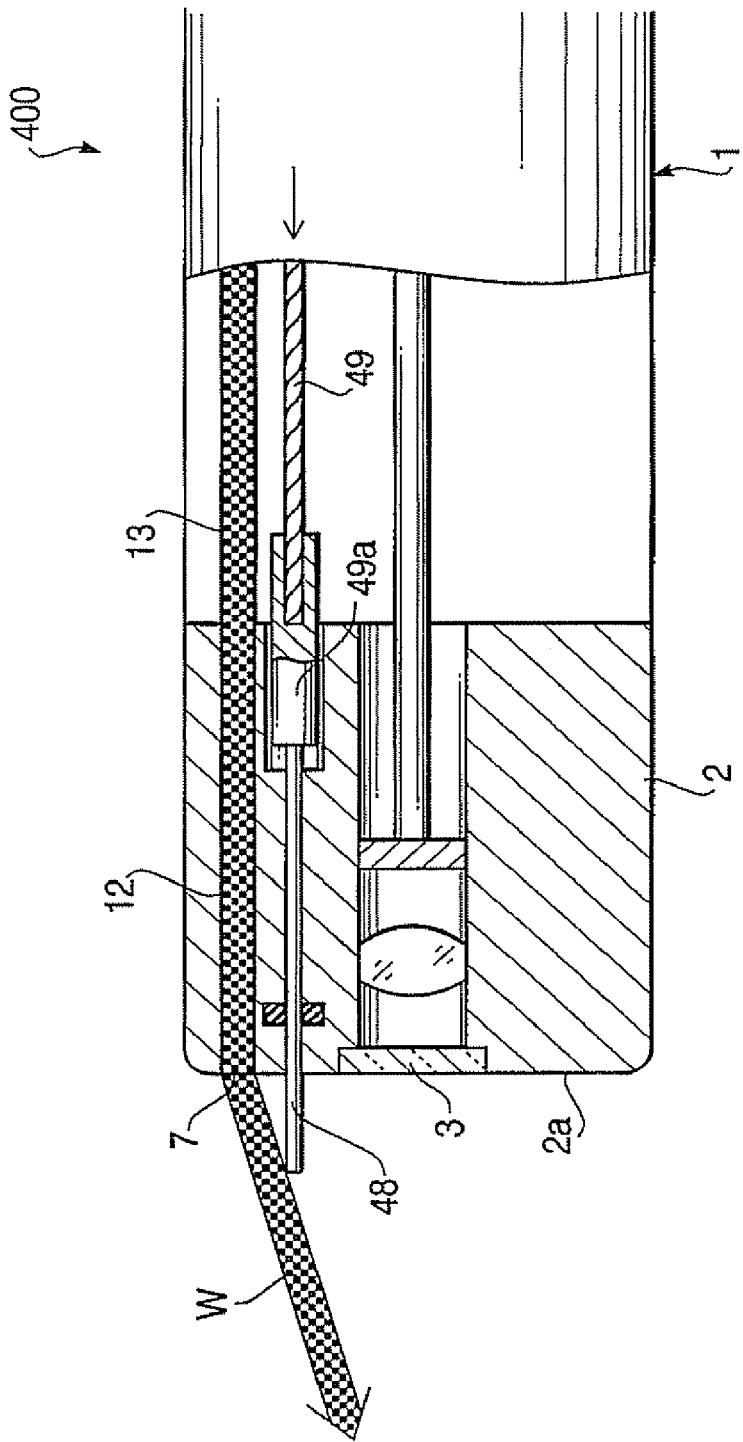
FIG. 13 shows a cross-sectional side view of the tip portion of the endoscope as a flow attracting pin is protruded to an extent according to the fourth embodiment of the invention.
Figure 14:
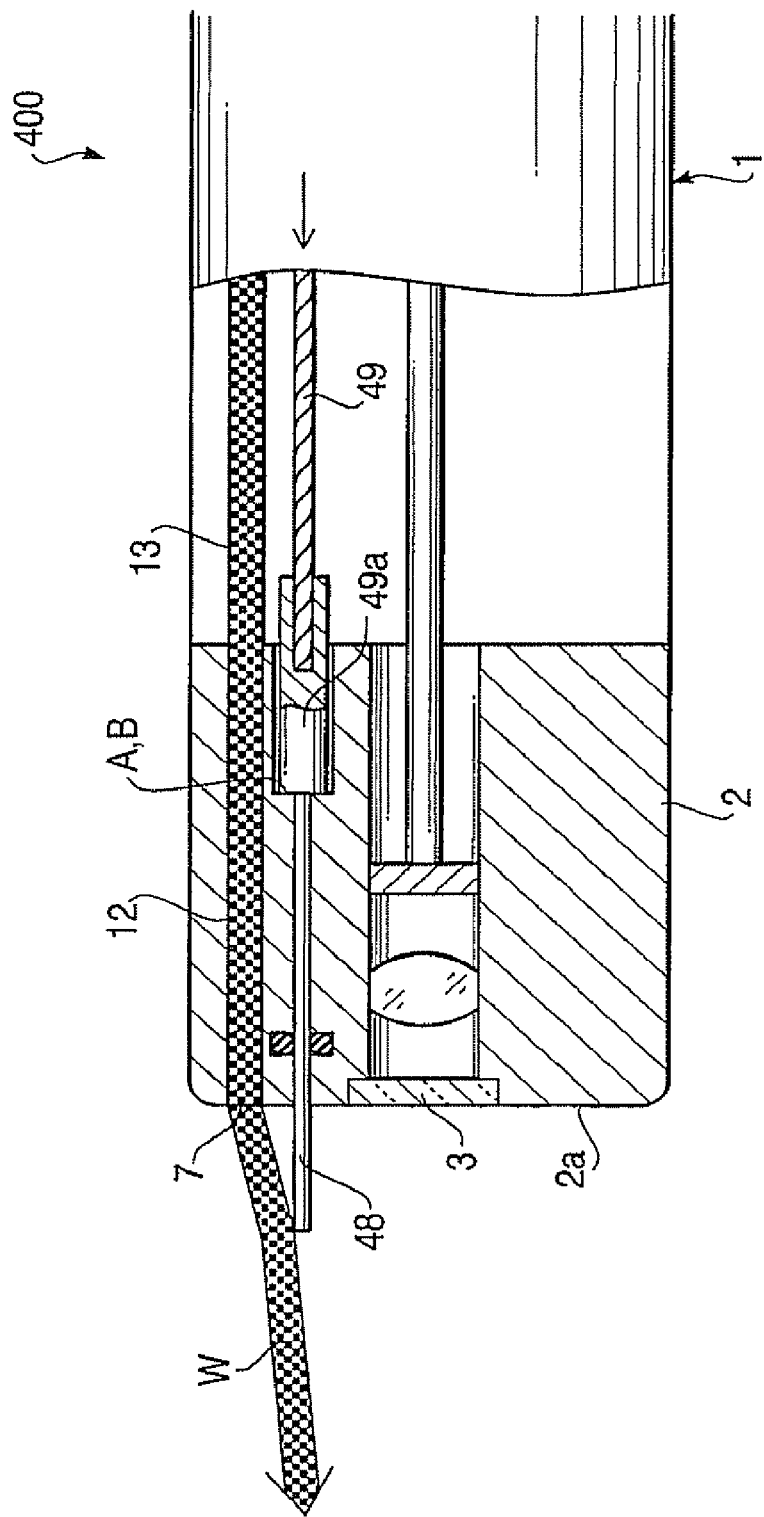
FIG. 14 shows a cross-sectional side view of the tip portion of the endoscope as the flow attracting pin is protruded to a maximum extent according to the fourth embodiment of the invention.

FIG. 13 shows a cross-sectional side view of the tip portion 2 of the endoscope 400 as the flow attracting pin 48 is protruded to an extent according to the fourth embodiment of the invention. FIG. 14 shows a cross-sectional side view of the tip portion 2 of the endoscope 400 as the flow attracting pin 48 is protruded to a maximum extent according to the fourth embodiment of the invention.

As the flow attracting pin 48 is protruded further from the distal surface 2a, as shown in FIG. 14, the effected water W flows at an acuter angle with respect to the flow attracting pin 48. When the flow attracting pin 48 is protruded to a maximum extent from the distal surface 2a, as shown in FIG. 14, the contact surface A and the stopper surface B become in contact with each other. In this state, the angle between the water W and the flow attracting pin 48 becomes the least and the water W flows on the flow attracting pin 48.

With the above configuration, the flow of the water W ejected from the liquid outlet 7 can be angled arbitrarily, so that the water W can be directed to the center of the observed region of the mucous membrane, which is to be cleaned.

Figure 21:
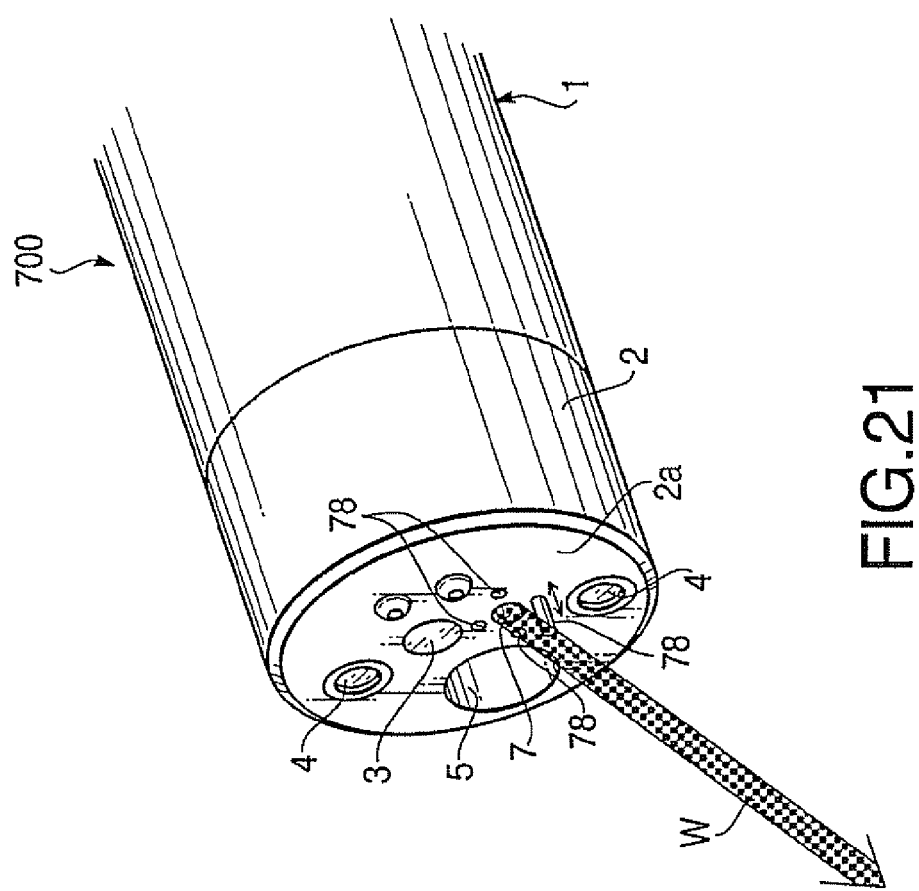
FIG. 21 shows a perspective view of a tip portion of an endoscope according to a seventh embodiment of the invention.

It should be noted that the number of the flow attracting pin 48 may not necessarily be one, but the tip portion 2 may be provided with a plurality of flow attracting pins that are arranged in vicinity to a liquid outlet 7 and selectively protruded by remote operation (see FIG. 21, for example).

Fifth Embodiment

Figure 15:
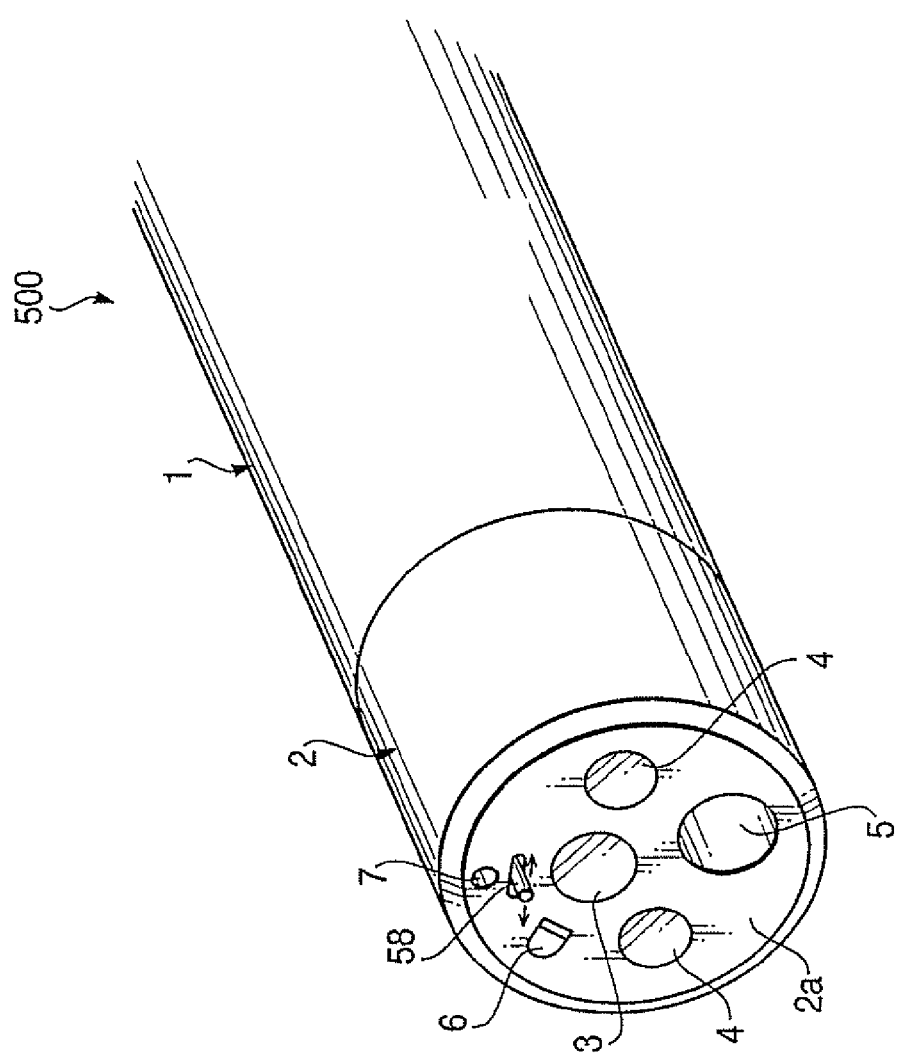
FIG. 15 shows a perspective view of a tip portion of an endoscope 500 according to a fifth embodiment of the invention.
Figure 16:
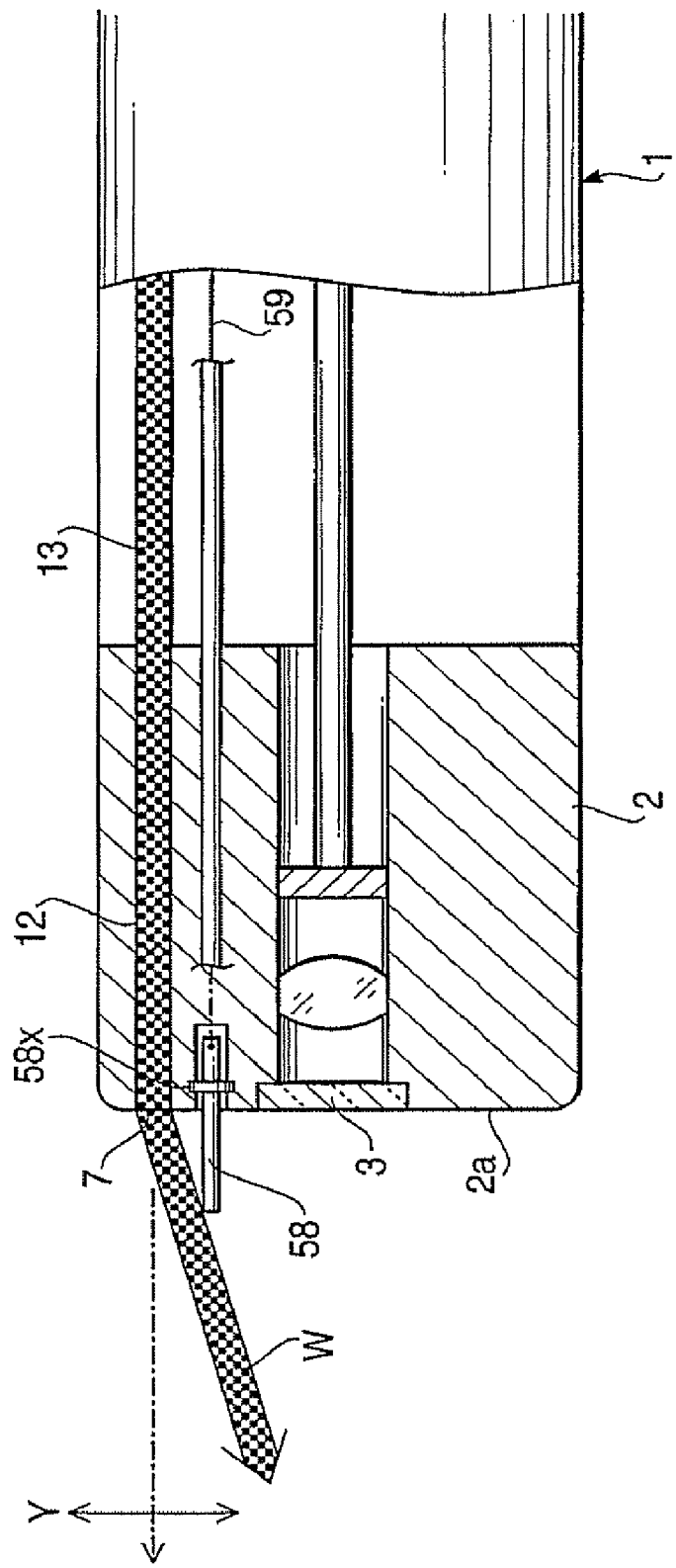
FIG. 16 shows a cross-sectional side view of the tip portion of the endoscope according to the fifth embodiment of the invention.

FIG. 15 shows a perspective view of a tip portion 2 of an endoscope 500 according to a fifth embodiment of the invention. FIG. 16 shows a cross-sectional side view of the tip portion 2 of the endoscope 500 according to the fifth embodiment of the invention. As shown in FIGS. 15 and 16, the flow attracting pin 58 is arranged adjacently to the liquid outlet 7 and in a position between the liquid outlet 7 and the observation window 3. The flow attracting pin 58 is configured to have a cross-section of a circle, and is adapted to be shifted in parallel with the distal surface 2a of the tip portion 2 by a remote operation.

The operation knob 51 (see also FIG. 1) is connected to an operation wire 59, which is arranged inside an inserted portion 1. The operation wire 59 is connected with a proximal end of the flow attracting pin 58, thus the operation to the operation knob 51 is conveyed to the flow attracting pin 58.

In the present embodiment, the flow attracting pin 58 is pivotably supported by a supporting shaft 58x, which is fixed inside the tip portion 2. The flow attracting pin 58 is configured to pivot about the supporting shaft 58x in a direction perpendicular to a line connecting a center of the liquid outlet 7 and a center of the observation window 3, as indicated by arrows in FIG. 15.

The flow attracting pin 58 is extended toward a proximal end of the tip portion 2. The operation wire 59 is connected perpendicularly to a proximal end of the flow attraction pin 58. Thus, as the operation wire 59 is operated in an axial direction, the flow attracting pin 58 is pivoted about the supporting shaft 58x, and is shifted in the direction perpendicular to the line connecting the center of the liquid outlet 7 and the center of the observation window 3.

With the above configuration, when the flow attracting pin 58 is directed to an approximately straight front thereof (perpendicularly to the distal surface 2a), as shown in FIG. 16, water W ejected from the liquid outlet 7 is attracted to the flow attracting pin 58, which is protruded from the distal surface 2a, and the water W is directed toward a distal end of the flow attracting pin 58 (i.e., the water W is angled to flow in front of the observation window 3).

Figure 17:
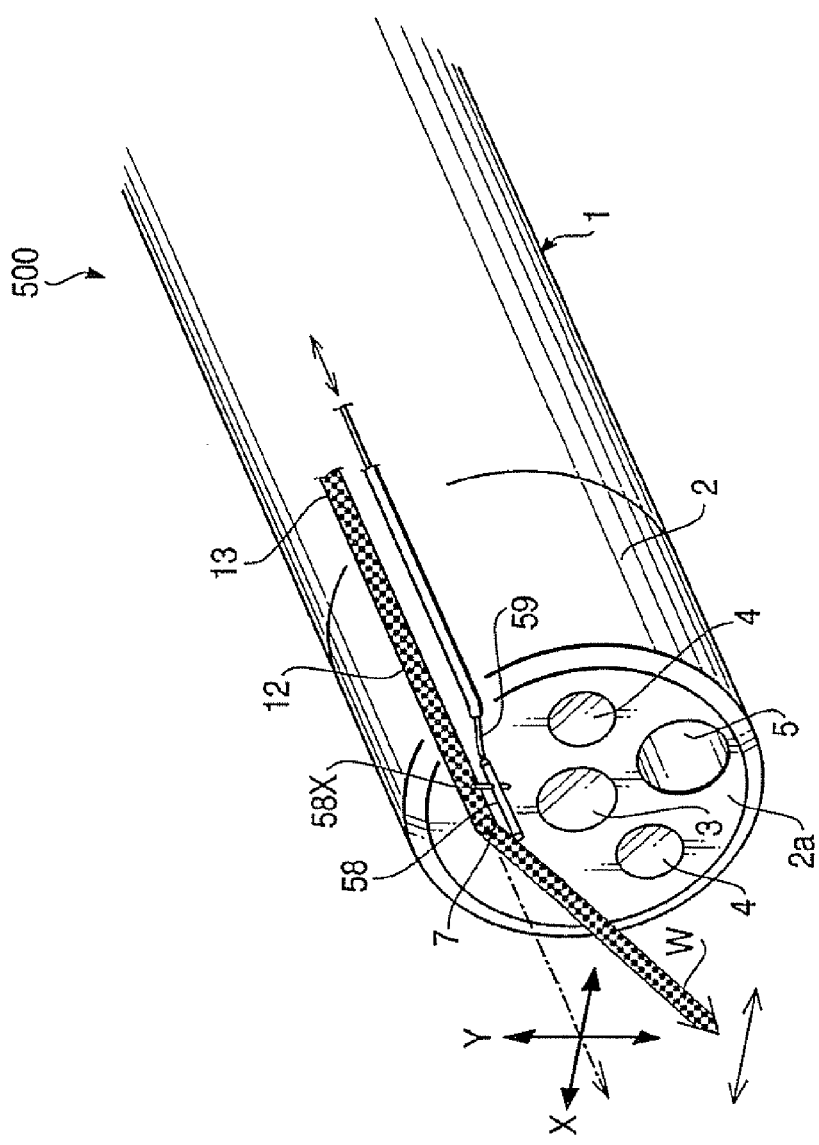
FIG. 17 shows a perspective view of the tip portion of the endoscope when water is ejected from a liquid outlet according to the fifth embodiment of the invention.

FIG. 17 shows a perspective view of the tip portion 2 of the endoscope 500 when the water W is ejected from the liquid outlet 7 according to the fifth embodiment of the invention. The flow attracting pin 58 is directed to a straight front of the line connecting the center of the liquid outlet 7 and the center of the observation window 3. In this state, the flow of the water W is angled only in a Y direction in an X-Y coordinate, which is indicated in FIG. 18.

Figure 18:
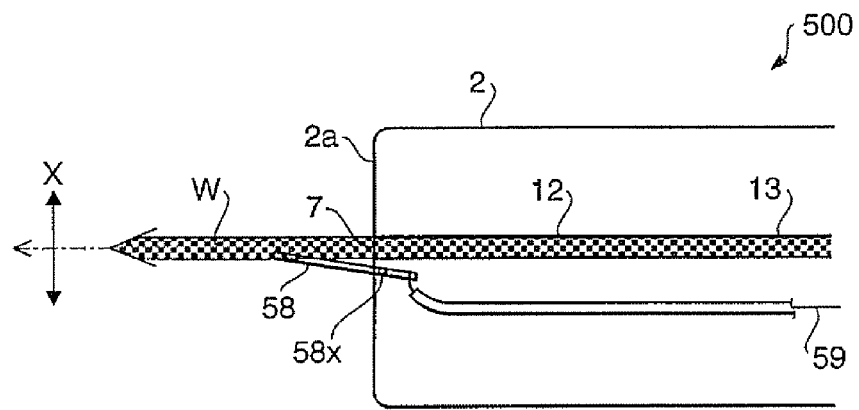
FIGS. 18 and 19 show cross-sectional upper side views of the tip portion of the endoscope according to the fifth embodiment of the invention.
Figure 19:
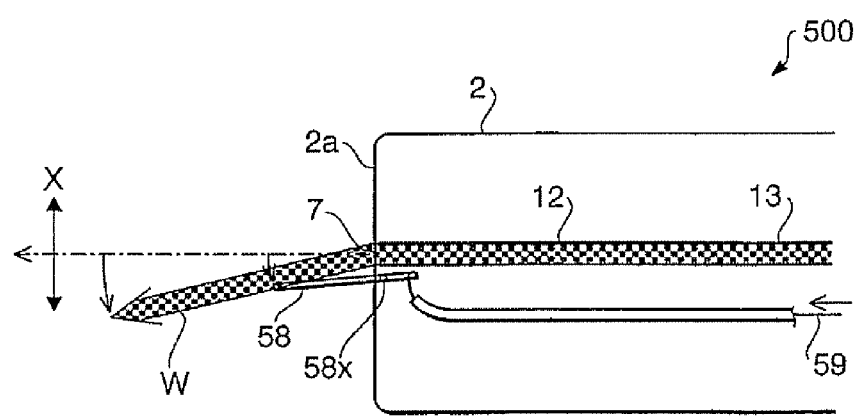

FIGS. 18 and 19 show cross-sectional upper side views of the tip portion 2 of the endoscope 500 according to the fifth embodiment of the invention. When the operation wire 59 is operated (retracted or forwarded) from a position indicated in FIG. 18, and the flow attracting pin 58 is pivoted about the supporting shaft 58x, as shown in FIG. 19, the distal end of the flow attracting pin 58 is shifted in the direction in parallel with the distal surface 2a. In this state, the flow of the water W, which has been angled in the Y direction, is shifted in correspondence to the flow attracting pin 58 in an X direction.

In this configuration, the direction of the ejected water W can be adjusted, and an aimed portion of the mucous membrane can be effectively cleaned during observation without having the entire inserted portion 1 of the endoscope 500 moved.

Sixth Embodiment

Figure 20:
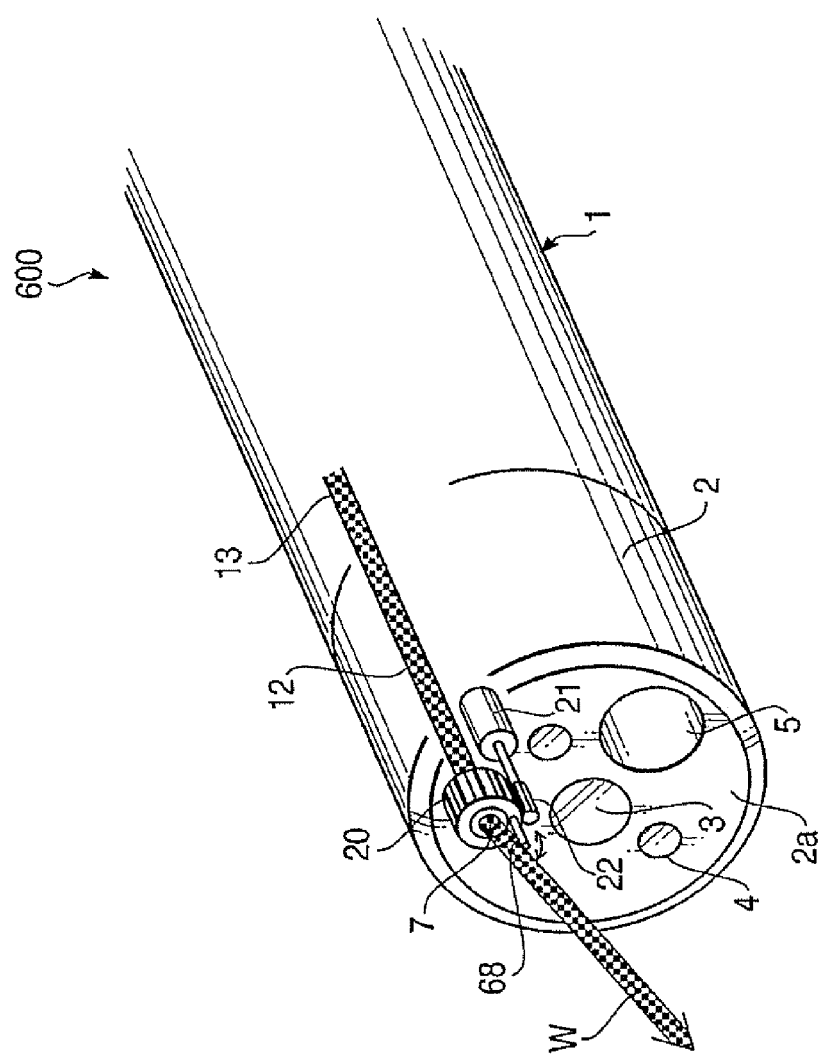
FIG. 20 shows a perspective view of a tip portion of an endoscope according to a sixth embodiment of the invention.

FIG. 20 shows a perspective view of a tip portion 2 of an endoscope 600 according to a sixth embodiment of the invention. In the present embodiment, a flow attracting pin 68, protruding perpendicularly to a distal surface 2a, is fixedly arranged on a greater gear 20, which is adapted to rotate about a center of a liquid outlet 7. The greater gear 20 is engaged with an output gear 22, which is rotated by a micromotor 21. When the micromotor 21 is activated and the output gear 21 is rotated, the greater gear 20 is also rotated, so that the flow attracting pin 68 is rotated about the center of the liquid outlet 7 with an orientation thereof maintained perpendicular to the distal surface 2a. Thus, a direction of the ejected water W can be adjusted, and an aimed portion of the mucous membrane can be effectively cleaned during observation without having the entire inserted portion 1 of the endoscope 600 moved.

Seventh Embodiment

FIG. 21 shows a perspective view of a tip portion 2 of an endoscope 700 according to a seventh embodiment of the invention. It should be noted that a plurality of protrusive flow attracting pins 78 are arranged in vicinity to a liquid outlet 7. In the present embodiment, four flow attracting pins 78 are provided around the liquid outlet 7, with an interval of approximately 90 degrees between each other.

As one of the four flow attracting pins 78 is selected and protruded from a distal surface 2a by a remote operation, a direction of the ejected water W is changed, and an aimed portion of the mucous membrane can be effectively cleaned during observation without having the entire inserted portion 1 of the endoscope 700 moved. In this configuration, tie flow attracting pins 78 serve as the flow attracting pin 68 of the sixth embodiment when the flow attracting pin 68 is rotated in a phased manner. It should be noted that two or more of the four flow attracting pins 78 may be configured to be simultaneously protruded from the distal surface 2a to change the direction of the ejected water W.

Eighth Embodiment

Figure 22:
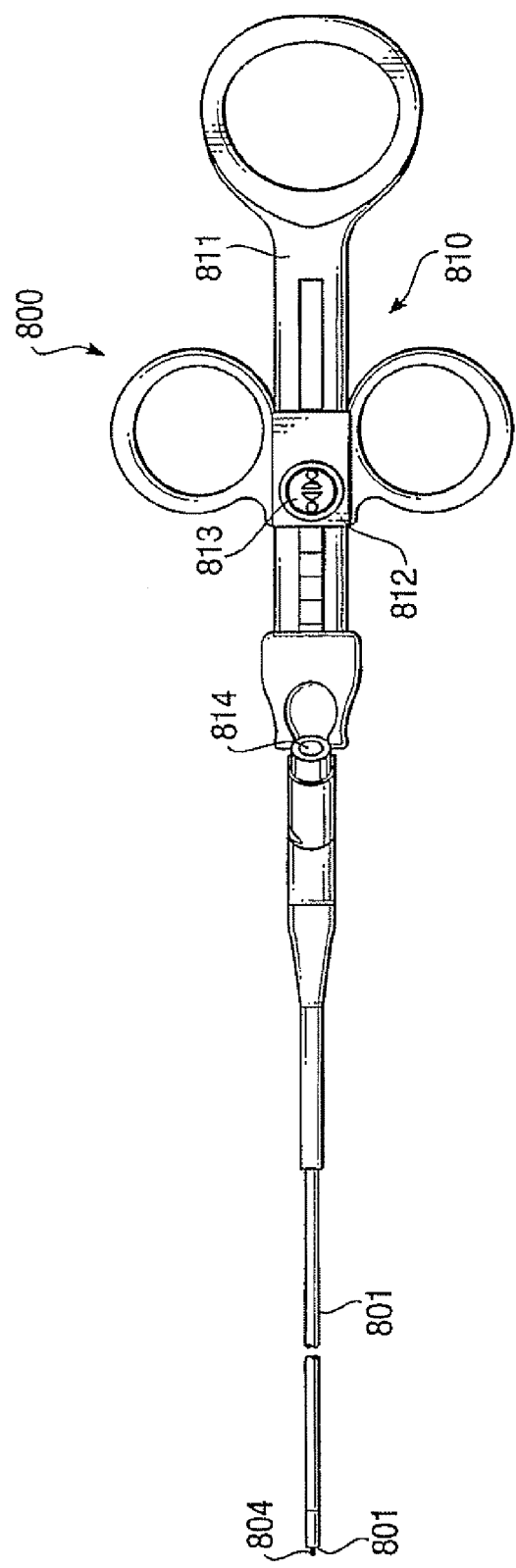
FIG. 22 shows a plane view of an entire configuration of a treatment tool for an endoscope according to an eighth embodiment of the invention.
Figure 23:
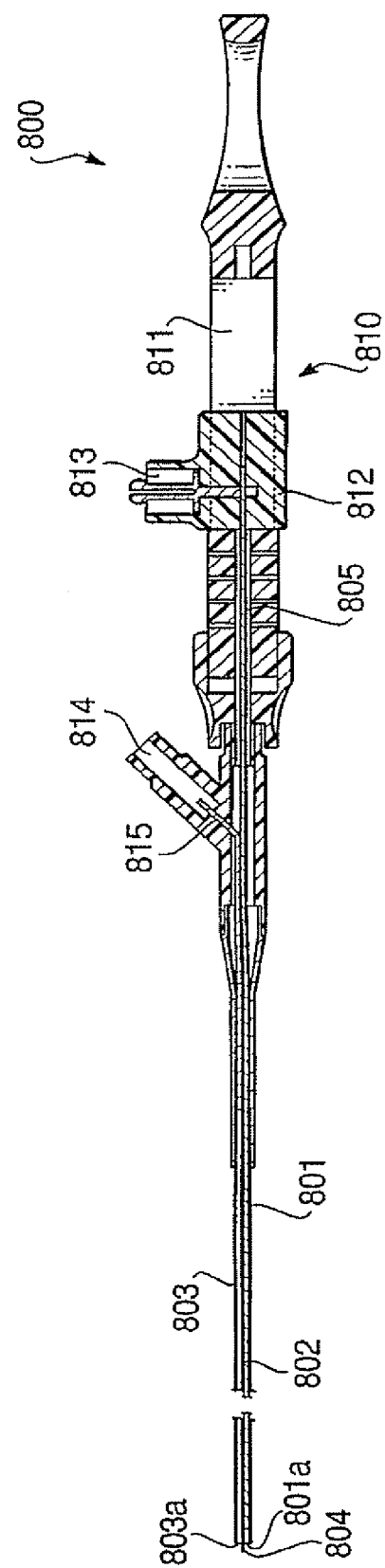
FIG. 23 shows a cross-sectional side view of the entire configuration of the treatment tool according to the eighth embodiment of the invention.

FIG. 22 shows a plane view of an entire configuration of a treatment tool 800 for an endoscope according to an eighth embodiment of the invention. FIG. 23 shows a cross-sectional side view of the entire configuration of the treatment tool 800 according to the eighth embodiment of the invention.

The treatment tool 800 includes a flexible tubular sheath 801, which is made of an electrically insulated material, for example polytetrafluoroethylene, and has a length ranging for example from approximately 1 to 2 meters, and a diameter being approximately 2 millimeters. The sheath 801 includes a distal surface 801a, and is adapted to be inserted through an instrument channel (not shown) of the endoscope.

The sheath 801 is formed to be a multi-lumen tube having a plurality of (for example, two) independent lumens, which are a wire lumen 802 and a liquid channel 803, formed in parallel with each other through the entire length of the sheath 801.

Figure 24:
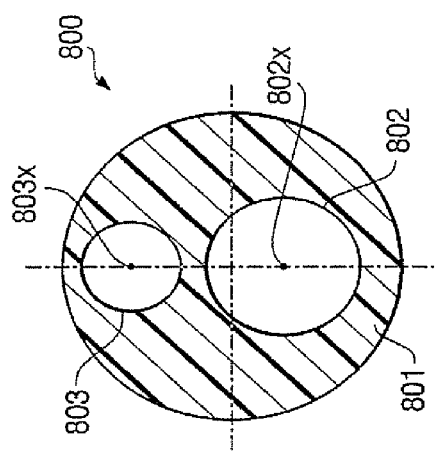
FIG. 24 shows a cross-sectional view of a sheath, taken along a line perpendicular to an axis of the sheath, according to the eighth embodiment of the invention.

FIG. 24 shows a cross-sectional view of the sheath 801, taken along a line perpendicular to an axis of the sheath 801, according to the eighth embodiment of the invention. The wire lumen 802 is arranged in a position where an axis 802x thereof is eccentric to an axis 801x of the sheath 801. Similarly, the liquid channel 803 is arranged in a position where an axis 803x thereof is eccentric to the axis 801x of the sheath 801. Diameters of the wire lumen 802 and the liquid channel 803 are constant throughout the entire the sheath 801. The axis 801x of the sheath 801 is included in the wire lumen 802.

As shown in FIGS. 22 and 23, at a distal portion of the sheath 801, a rod-like high-frequency electrode 804 is provided, and is configured to be protruded outwardly and retracted inwardly by an operation from a user via an operation unit 810, which is provided at a proximal end of the sheath 801.

Further, an operation wire 805 (which is an electrically conductive wire made of, for example, one of stainless steel) is inserted over the entire length of the sheath 801. The operation wire 805 is movable along the axis 801x of the sheath 1

(i.e., in the axial direction of the sheath 1), and the electrode 804 is connected to a distal end of the operation wire 805.

The operation unit 810 includes an operation shaft 801, which is connected to the proximal end of the sheath 801, and a slidable portion 812, which is adapted to slide along the axial direction of the operation unit 810. The slidable portion 812 is connected with a proximal end of the operation wire 805. With this configuration, the electrode 804 can be protruded and retracted from the distal portion of the sheath 801 by the operation from the user. The slidable portion 812 is provided with a power terminal 13, to which a power supplying cable (not shown) is connected, so that electrical current with high-frequency can be supplied to the high-frequency electrode 804 via the operation wire 805.

On a proximal end of the liquid channel 803, a liquid filler port 814 is provided, so that liquid to be used for cleaning a region of a mucous membrane is injected therethrough and is ejected from a liquid outlet 803a toward a front of a distal portion of the treatment tool 800.

Figure 25:
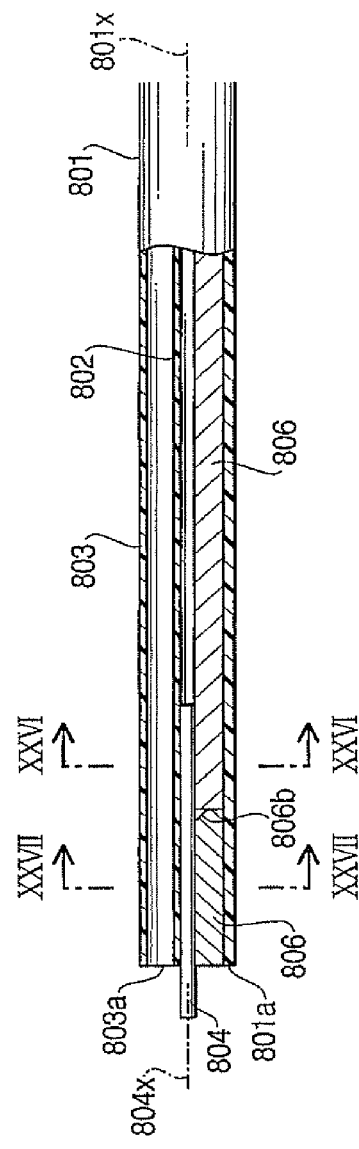
FIG. 25 shows a cross-sectional side view of a tip portion of the treatment tool according to the eighth embodiment of the invention.
Figure 26:
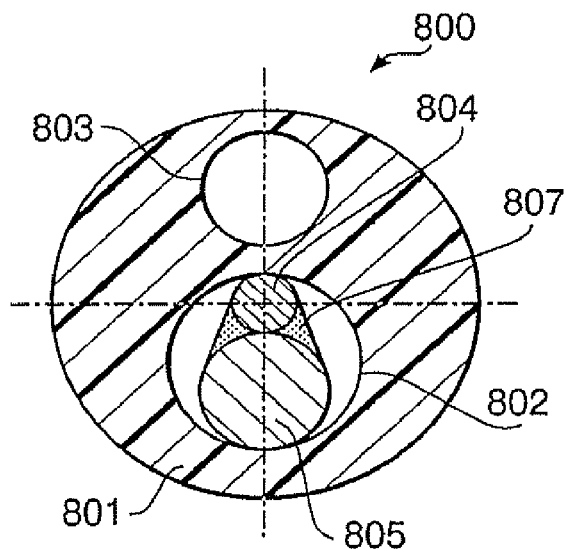
FIG. 26 shows a cross-sectional view of the tip portion of the treatment tool taken along the line XXVI-XXVI in FIG. 25 according to the eighth embodiment of the invention.
Figure 27:
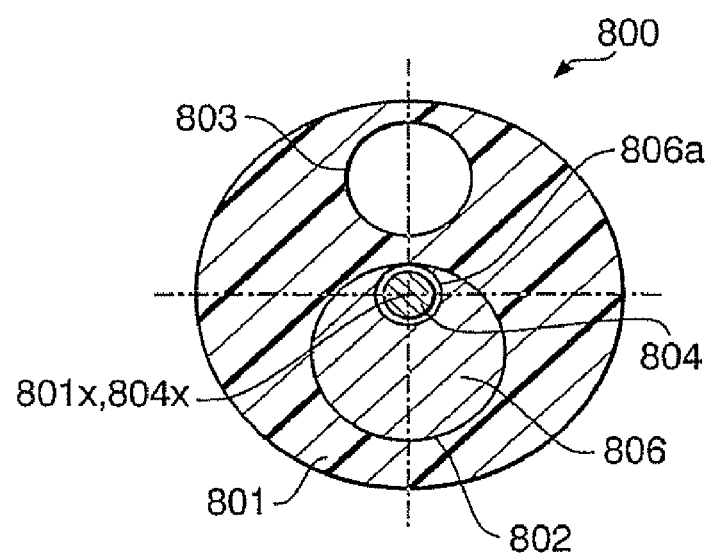
FIG. 27 shows a cross-sectional view of the tip portion of the treatment tool taken along the line XXVII-XXVII in FIG. 25 according to the eighth embodiment of the invention.

FIG. 25 shows a cross-sectional side view of a tip portion of the treatment tool 800 according to the eighth embodiment of the invention. FIG. 26 shows a cross-sectional view of the tip portion of the treatment tool 800 taken along the line XXVI-XXVI in FIG. 25 according to the eighth embodiment of the invention, and FIG. 27 shows a cross-sectional view of the tip portion of the treatment tool 800 taken along the line XXVU-XXVH in FIG. 25 according to the eighth embodiment of the invention. Further, FIG. 28 shows a perspective view of the high-frequency electrode 804 connected with the operation wire 805 according to the eighth embodiment of the invention.

The high-frequency electrode 804 is made of electrically conductive metal such as stainless-steel. In the present embodiment, a tip end of the high-frequency electrode 804 is formed to be obtuse, however, the tip end is not necessarily be obtuse, but may be formed to be sharp, or may have a form of a pipe, for example.

Figure 28:
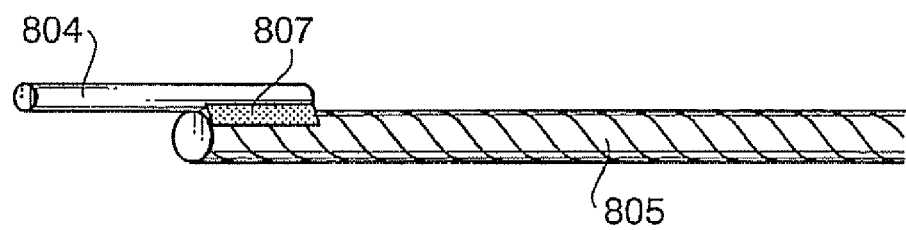
FIG. 28 shows a perspective view of a high-frequency electrode connected with an operation wire according to the eighth embodiment of the invention.

As shown in FIG. 28, the high-frequency electrode 804 is connected with a distal end of the operation wire 805. A part of a circumferential surface of the high-frequency electrode 804 is bonded to a circumferential surface of the distal end of the operation wire 805 by silver blazing 7, for example, so that the high-frequency electrode 804 and the operation wire 805 are aligned in parallel with each other. With this configuration, the connecting portion of the high-frequency electrode 804 and the operation wire 805 can be effectively arranged in the wire lumen 802 of the sheath 801, as shown in FIG. 26.

When the high-frequency electrode 804 as described above is protruded and retracted from the distal surface 801a by operations to the operation wire 805, the distal end of the high-frequency electrode 804 may be easily fluctuated in various directions, and the fluctuated high-frequency electrode 804 may cause trouble to the user. Therefore, in the present embodiment, in order to overcome the inconvenience, the sheath 801 is provided with an electrode restricting member 806, which is adapted to restrict the fluctuation of the high-frequency electrode 804. As shown in FIG. 27, an electrode restricting member 806 is fixedly arranged inside the wire lumen 802 at the distal portion.

Figure 29:
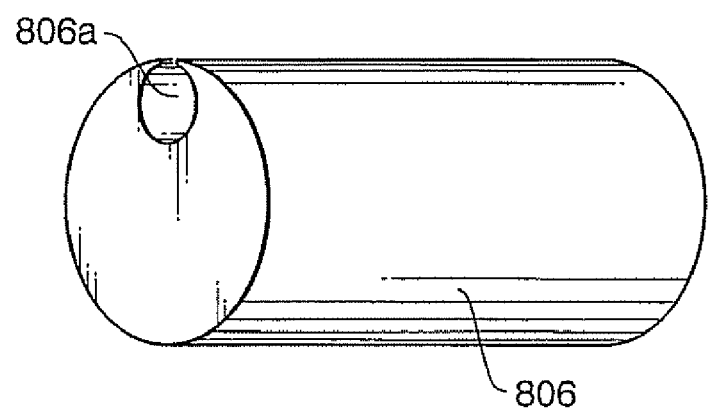
FIG. 29 shows a perspective view of an electrode restricting member for the treatment tool according to the eighth embodiment of the invention.

FIG. 29 shows a perspective view of the electrode restricting member 806 for the treatment tool 800 according to the eighth embodiment of the invention. The electrode restricting member 806 is formed to have a shape of a cylinder, and a circumferential surface thereof is adapted to be tightly fit into an inner surface of the wire lumen 802. Further, a guide hole 806a (an instrument outlet) is formed in the electrode restricting member 806, in vicinity to the circumferential surface of the electrode restricting member 806, with an axis there of being in parallel to an axis of the electrode restricting member 806. The guide hole 806 is configured to have a diameter that allows only the high-frequency electrode 804 to be protruded and retracted therethrough, whilst the operation wire 805 is not allowed to be inserted therethrough. With this configuration, the high-frequency electrode 804 can be forwarded and retracted from the distal surface 801a through the guide hole 806a without being fluctuated.

The guide hole 806a is formed to have an axis thereof to correspond to the axis $801x$ of the sheath 801 when the electrode restricting member 806 is inserted in the distal portion of the wire lumen a02. With this configuration, as the high-frequency electrode 804 is positioned in the guide hole 806a, an axis $804x$ of the high-frequency electrode 804 corresponds to the axis $801x$ of the sheath 801 (see FIG. 27).

Figure 30:
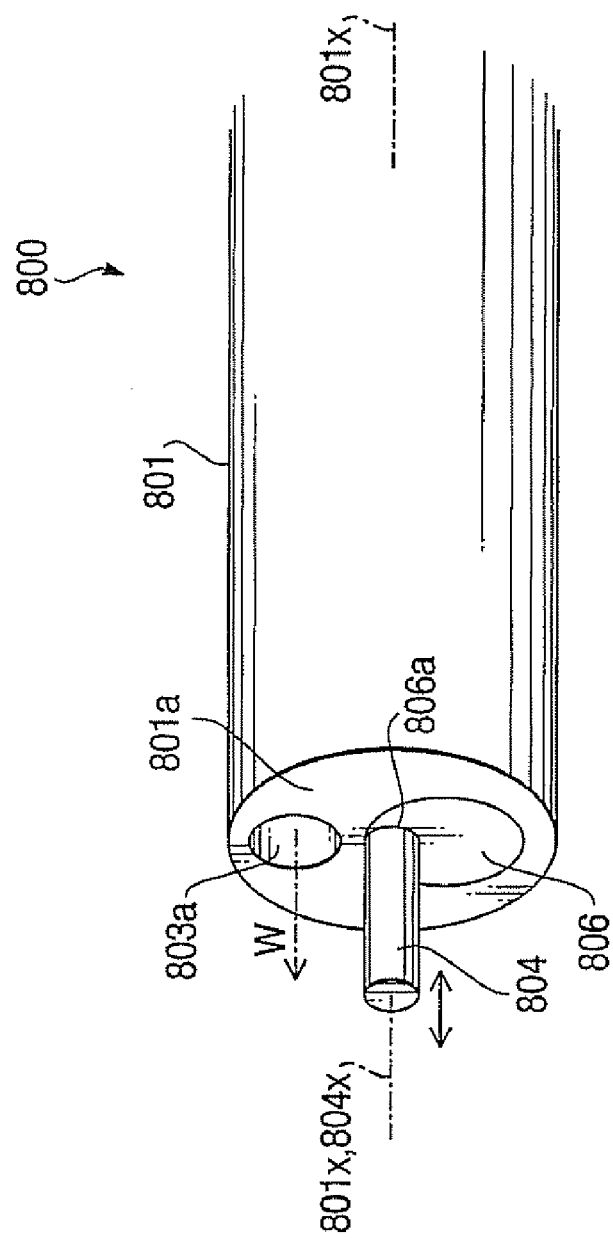
FIG. 30 shows a perspective outer view of the tip portion of the treatment tool according to the eighth embodiment of the invention.

FIG. 30 shows a perspective outer view of the tip portion of the treatment tool 800 according to the eighth embodiment of the invention. As the operation wire 805 is forwarded and retracted by the operations to the operation unit 810, the high-frequency electrode 804 is protruded and retracted from a position corresponding to the axis $80lx$ on the distal surface 801a of the sheath 801 without being fluctuated. It should be noted that a maximum allowable length of the high-frequency to be protruded from the distal surface 801a is restricted as the distal end of the operation wire 805 becomes in contact with a proximal surface 806b of the electrode restricting member 806 (see FIG. 25).

In the treatment tool 800 as configured above, it should be noted that a cross-sectional area of the liquid channel 803 has a shape of a circle, and the liquid outlet 803a opened at the distal end of the liquid channel 803 has a shape of the circle as well, so that water W is ejected therefrom as indicated in a dotted arrow in FIG. 30.

Figure 31:
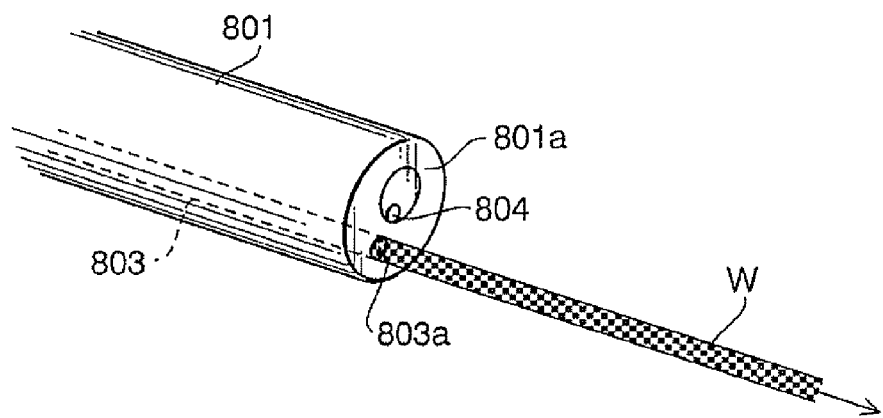
FIG. 31 shows a perspective view of the tip portion of the treatment tool when water is ejected toward a straight front according to the eighth embodiment of the invention.
Figure 32:
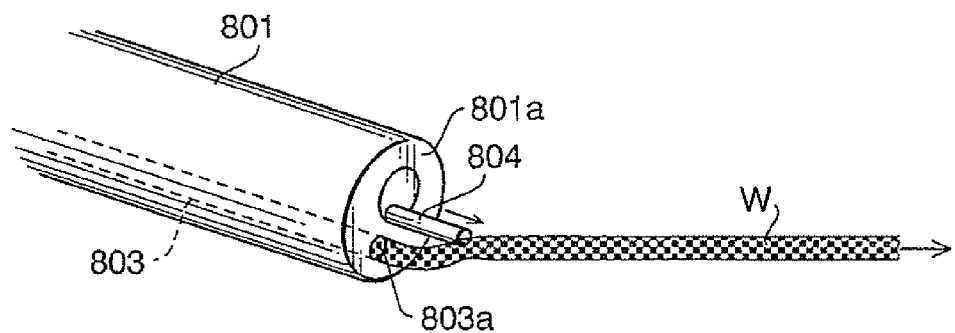
FIG. 32 shows a perspective view of the tip portion of the treatment tool when a flow of the water is angled according to the eighth embodiment of the inventions

FIG. 31 shows a perspective view of the tip portion of the treatment tool 800 when the water W is ejected toward a straight front according to the eighth embodiment of the invention, FIG. 32 shows a perspective view of the tip portion of the treatment tool 800 when a flow of the water W is angled according to the eighth embodiment of the invention.

As shown in FIG. 31, when the high-frequency electrode 804 is retracted in the sheath 801, the water W ejected from the liquid outlet 803a is directed to the straight front, and a diameter of the water W corresponding to the diameter of the liquid outlet 803a is maintained steady until the water W strikes a portion of a mucous membrane to be cleaned.

When the high-frequency electrode 804 is protruded from the distal surface 803a, as shown in FIG. 32, the flow of the water W ejected from the liquid outlet 803a is attracted to the high-frequency electrode 804, and is angled toward a predetermined position of the mucous membrane to be cleaned. It should be noted that also in this state, the diameter of the water W corresponding to the diameter of the liquid outlet 803a is maintained steady until the water W strikes the portion of the mucous membrane to be cleaned. It should be further noted that the high-frequency electrode 804 in the present embodiment serves as the flow attracting members described in the previous embodiments.

With the above configuration, as the direction of the ejected water W can be modified, the water W can be aimed at the portion to be cleaned without having the entire treatment tool 800 shifted. Furthermore, even in an endoscope unit with a high-frequency treatment tool, of which diameter is approximately from 2 to 3 mm, the flow of the water W can be angled at a predetermined direction.

Although examples of carrying out the invention have been described, those skilled in the art will appreciate that there are numerous variations and permutations of the flow attracting member and the endoscope that fall within the spirit and scope of the invention as set forth in the appended claims. It is to be understood that the subject matter defined in the appended claims is not necessarily limited to the specific features or act described above. Rather, the specific features and acts described above are disclosed as example forms of implementing the claims.

For example, as the water is ejected from the liquid outlet, in the first through the seventh embodiments, the angled water may be directed to the other direction than the direction toward the front of the observation window. For another example, in the eighth embodiment, the high-frequency electrode may not necessarily be fully included in the sheath as the high-frequency electrode is retracted, but may be retracted substantially so that the flow of the water may not be attracted to the high-frequency electrode.

The present disclosure relates to the subject matter contained in Japanese Patent Applications No. P2005-169033, filed on Jun. 9, 2005, Nos. P2005-171936 and P2005-171937, filed on Jun. 13, 2005, and No. P2005-173152, filed on Jun. 14, 2005, which are expressly incorporated herein by reference in their entireties.

What is claimed is:

1. An endoscope, comprising:
   an inserted portion, which is adapted to be inserted into an organ, having a distal portion with a distal surface;
   a liquid outlet, which is formed on the distal surface of the distal portion, and is adapted to eject liquid therefrom toward an object located in vicinity to the distal portion, the liquid outlet opening to a straight front of the distal surface of the inserted portion; and
   a flow attracting member, formed as a cylindrical pin, which is adapted to attract a flow of the liquid ejected from the liquid outlet,
   wherein the flow of the liquid ejected from the liquid outlet is angled by the flow attracting member so that the liquid is directed at a predetermined portion of the object,
   wherein the flow attracting member is formed as a pin arranged in the distal portion at a position adjacent to the liquid outlet so as to protrude forwardly from the distal surface of the inserted portion, and the flow attracting member is fixed against pivoting movement at the distal surface of the inserted portion, and
   wherein the liquid outlet is positioned at an axially spaced location from the flow attracting member.

2. The endoscope according to claim 1, wherein the liquid outlet is oriented in parallel with an axis of the inserted portion.

3. The endoscope according to claim 1,
   wherein the distal surface of the inserted portion is provided with an observation window to capture an image of the object, and
   wherein the flow attracting member is arranged on the distal surface of the inserted portion in a position between the liquid outlet and the observation window, so that the liquid ejected from the liquid outlet is attracted to the flow attracting member and the flow of the liquid can be angled toward a front of the observation window.

4. The endoscope according to claim 1,
   wherein the flow attracting member is adapted to be protrusible and retractable in an axial direction of the inserted portion, so that a flow of the liquid ejected from the liquid outlet is angled in correspondence to protrusion and retraction of the flow attracting member.

5. The endoscope according to claim 4, wherein the flow attracting member is adapted to be protruded and retracted by a remote operation.

6. The endoscope according to claim 5,
   wherein the distal surface of the inserted portion is provided with an observation window to capture an image of the object, and
   wherein the flow attracting member is arranged on the distal surface of the inserted portion in a position between the liquid outlet and the observation window, so that the liquid ejected from the liquid outlet is attracted to the flow attracting member and the flow of the liquid can be angled toward a front of the observation window.

7. The endoscope according to claim 5, wherein the flow attracting member is formed to be a protrusible pin to be protruded forwardly and retracted inwardly from the distal surface of the inserted portion.

8. The endoscope according to claim 4,
   wherein the flow attracting member includes a plurality of pins arranged in vicinity to the liquid outlet, and
   wherein at least one of the plurality of pins is selectively protruded and retracted from the distal surface of the inserted portion.

9. The endoscope according to claim 1,
   wherein the flow attracting member is adapted to be shifted along the distal surface of the inserted portion so that a flow of the liquid ejected from the liquid outlet is shifted in correspondence to movements of the flow attracting member.

10. The endoscope according to claim 9, wherein the flow attracting member is adapted to rotate about an axis.

11. The endoscope according to claim 9, wherein the flow attracting member is adapted rotate around the liquid outlet.

12. The endoscope according to claim 9,
    wherein the flow attracting member includes a plurality of pins arranged in vicinity to the liquid outlet, and
    wherein at least one of the plurality of pins is selectively protruded and retracted from the distal surface of the inserted portion.

13. The endoscope according to claim 9, wherein the flow attracting member is shifted by a remote operation to an operation wire, which is adapted to be forwarded and retracted.

14. The endoscope according to claim 9, wherein the flow attracting member is shifted by drive force from a motor equipped in the distal portion.

15. The endoscope according to claim 1, further comprising:
    a treatment tool having a sheath to be inserted through an insertion channel of the endoscope, and a rod-like high-frequency electrode, which is adapted to be protrusible and retractable in an axial direction of the sheath from a distal surface of the sheath,
    wherein the high-frequency treatment tool is adapted to serve as the flow attracting member, and the flow of the liquid ejected from the liquid outlet is angled by the high-frequency electrode when the high-frequency electrode is protruded from the distal surface of the sheath.

16. The endoscope according to claim 15,
    wherein the liquid outlet is arranged adjacent to the high-frequency electrode with a predetermined distance therebetween.

17. The endoscope according to claim 15,
    wherein the flow of the liquid ejected from the liquid outlet is directed toward a straight front of the liquid outlet when the high-frequency electrode is retracted from the distal surface of the sheath.

18. The endoscope according to claim 15, wherein a distance on the distal surface between the liquid outlet and the high-frequency electrode is 0.5 mm at a maximum.

19. The endoscope according to claim 18, wherein the distance on the distal surface between the liquid outlet and the high-frequency electrode is in a range from 0.3 mm to 0.5 mm.

20. The endoscope according to claim 15,
wherein a liquid channel to convey the liquid being ejected from the liquid outlet is formed in the sheath in parallel with an axis of the sheath,
wherein a diameter of the liquid channel is configured to be constant in a distal portion of the sheath, and
wherein the liquid channel is in communication with the liquid outlet, which is oriented in parallel with the axis of the sheath.

21. The endoscope according to claim 20,
wherein the sheath is configured to be a flexible multi-umen tube including a plurality of lumens, which are formed to extend in parallel with the axis of the sheath throughout an entire length of the sheath, and
wherein one of the plurality of lumens is adapted to be the liquid channel.

22. The endoscope according to claim 1, wherein a distance on the distal surface between the liquid outlet and the flow attracting member is 0.5 mm at a maximum.

23. The endoscope according to claim 22, wherein the distance on the distal surface between the liquid outlet and the flow attracting member is in a range from 0.3 mm to 0.5 mm.

24. The endoscope according to claim 1, further comprising the flow attracting member having a cross-section of a circle in a direction extending parallel to the distal surface of the inserted portion, and wherein the flow attracting member protrudes in a direction perpendicular to the distal surface of the inserted portion.

* * * * *